United States Patent
Su et al.

(10) Patent No.: US 9,730,027 B2
(45) Date of Patent: Aug. 8, 2017

(54) BACK-FILLING OF GEOLOCATION-BASED EXERCISE ROUTES

(71) Applicant: Fitbit, Inc., San Francisco, CA (US)

(72) Inventors: Hao-Wei Su, Cambridge, MA (US); Eric Foxlin, Lexington, MA (US); Subramaniam Venkatraman, Walnut Creek, CA (US); Logan Niehaus, Alameda, CA (US); Peter Duyan, San Francisco, CA (US); Shelten Gee Jao Yuen, Berkeley, CA (US); Timothy M. Roberts, San Francisco, CA (US)

(73) Assignee: Fitbit, Inc., San Francisco, CA (US)

(*) Notice: Subject to any disclaimer, the term of this patent is extended or adjusted under 35 U.S.C. 154(b) by 0 days.

(21) Appl. No.: 15/159,748

(22) Filed: May 19, 2016

(65) Prior Publication Data

US 2016/0269868 A1 Sep. 15, 2016

(51) Int. Cl.
 *G06F 17/40* (2006.01)
 *G01C 17/00* (2006.01)
 (Continued)

(52) U.S. Cl.
 CPC .......... *H04W 4/028* (2013.01); *G01C 22/006* (2013.01); *H04B 1/385* (2013.01); (Continued)

(58) Field of Classification Search
 CPC ..... H04W 4/028; G01C 22/006; G01C 21/20; H04M 1/72572
 (Continued)

(56) References Cited

U.S. PATENT DOCUMENTS

| 8,684,900 B2 | 4/2014 | Tran |
| 8,764,651 B2 | 7/2014 | Tran |

(Continued)

FOREIGN PATENT DOCUMENTS

| WO | WO 2012/170586 | 12/2012 |
| WO | WO 2012/170924 | 12/2012 |

(Continued)

OTHER PUBLICATIONS

DC Rainmaker, May 16, 2016, Hands-on with Garmin's new Vivosmart HR+ (now with GPS), http://www.dcrainmaker.com/2016/05/garmin-vivosmart-hr-now-with-gps.html, 34 pp.

(Continued)

*Primary Examiner* — Michael Nghiem
(74) *Attorney, Agent, or Firm* — Knobbe Martens Olson & Bear LLP

(57) ABSTRACT

Techniques for automatic tracking of user data for exercises are disclosed. In one aspect, a method of operating a wearable device may involve determining that a user of the wearable device has started an exercise, activating the GPS receiver in response to determining that the user has started the exercise, and detecting a time at which the GPS receiver achieves an initial GPS fix of a location of the wearable device. The method may further involve logging, based on output of the one or more biometric sensors, a first set of user data during a first time interval between the start of the exercise and the detected time of the initial GPS fix, and back-filling an exercise route of the user during the first time interval based on the first set of user data.

29 Claims, 13 Drawing Sheets

(51) Int. Cl.

| | |
|---|---|
| *G01C 19/00* | (2013.01) |
| *H04W 4/02* | (2009.01) |
| *H04W 4/00* | (2009.01) |
| *H04B 1/3827* | (2015.01) |
| *H04M 1/725* | (2006.01) |
| *G01C 22/00* | (2006.01) |
| *G01S 19/19* | (2010.01) |

(52) U.S. Cl.
CPC ... *H04M 1/72569* (2013.01); *H04M 1/72572* (2013.01); *H04W 4/008* (2013.01); *H04W 4/027* (2013.01); *G01S 19/19* (2013.01)

(58) Field of Classification Search
USPC .................................................. 702/150, 187
See application file for complete search history.

(56) References Cited

U.S. PATENT DOCUMENTS

| | | |
|---|---|---|
| 2007/0005243 A1 | 1/2007 | Horvitz |
| 2008/0287751 A1 | 11/2008 | Stivoric et al. |
| 2014/0180022 A1 | 6/2014 | Stivoric et al. |
| 2014/0200847 A1 | 7/2014 | Singiresu et al. |
| 2014/0278220 A1* | 9/2014 | Yuen ............ G01B 21/16 702/150 |
| 2014/0292564 A1* | 10/2014 | Park ............ G01S 19/09 342/357.2 |
| 2015/0026647 A1 | 1/2015 | Park et al. |
| 2015/0285659 A1 | 10/2015 | Curtis |
| 2016/0058337 A1 | 3/2016 | Blahnik |
| 2016/0263435 A1 | 9/2016 | Venkatraman |

FOREIGN PATENT DOCUMENTS

| | | |
|---|---|---|
| WO | WO 2012/171032 | 12/2012 |
| WO | WO 2015/127067 | 8/2015 |
| WO | WO 2016/003269 | 1/2016 |

OTHER PUBLICATIONS

Garmin Ltd., May 16, 2016, Garmin® introduces vivosmart® HR+, a smart activity tracker with wrist-based heart rate plus GPS, Press Release, 2 pp.

O'Kane, May 16, 2016, Garmin adds GPS to the Vivosmart Fitness tracker, The Verge, http://www.theverge.com/circuitbreaker/2016/5/16/11683116/garmin-vivosmart-hr-gps-fitness-tracker-wearable, 3 pp.

"Assisted GPS," (updated Mar. 31, 2014) in: Wikipedia, the free encyclopedia, [Retrieved on Apr. 2, 2014, downloaded at http://en.wikipedia.org/wiki/Assisted_GPS], 4 pages.

"Global Positioning System," (updated Mar. 29, 2014) in: Wikipedia, the free encyclopedia, [Retrieved on Apr. 2, 2014, downloaded at http://en.wikipedia.org/wiki/Global_Positioning_System], 23 pages.

"GPS navigation device," (updated Mar. 26, 2014) in: Wikipedia, the free encyclopedia, [Retrieved on Apr. 2, 2014, downloaded at http://en.wikipedia.org/wiki/GPS_navigation_device], 8 pages.

"GPS signals," (updated Apr. 1, 2014) in: Wikipedia, the free encyclopedia, [Retrieved on Apr. 2, 2014, downloaded at http://en.wikipedia.org/wiki/GPS_signals], 12 pages.

* cited by examiner

BACK-FILLING OF GEOLOCATION-BASED EXERCISE ROUTES

TECHNICAL FIELD

This disclosure relates to the field of wearable devices, and particularly to automatic tracking of geolocation data for exercises.

BACKGROUND

Consumer interest in personal health has led to a variety of personal health monitoring devices being offered on the market. Such devices, until recently, tended to be complicated to use and were typically designed for use with one activity, for example, bicycle trip computers.

Advances in sensors, electronics, and power source miniaturization have allowed the size of personal health monitoring devices, also referred to herein as "biometric tracking," "biometric monitoring," or simply "wearable" devices, to be offered in extremely small sizes that were previously impractical. The number of applications for these devices is increasing as the processing power and component miniaturization for wearable devices improves.

In addition, wearable devices may be used for the tracking of geolocation data, for example via a global positioning system (GPS) receiver. One application for the tracking of geolocation data is the logging of the route of an exercise performed by a user. The logging of geolocation data may require the GPS receiver to receive data from a plurality of GPS satellites.

SUMMARY

The systems, methods and devices of this disclosure each have several innovative aspects, no single one of which is solely responsible for the desirable attributes disclosed herein.

In one aspect, there is provided a method of operating a wearable device, the wearable device comprising one or more biometric sensors and a global positioning system (GPS) receiver. The method may involve: determining that a user of the wearable device has started an exercise; activating the GPS receiver in response to determining that the user has started the exercise; and detecting a time at which the GPS receiver achieves an initial GPS fix of a location of the wearable device. The method may further involve: logging, based on output of the one or more biometric sensors, a first set of user data relating to at least one of distance, direction, and speed of the user during a first time interval between the start of the exercise and the detected time of the initial GPS fix; and back-filling an exercise route of the user during the first time interval based on the first set of user data.

In another aspect, there is provided a wearable device that includes one or more biometric sensors, a GPS receiver, and at least one processor coupled to the one or more biometric sensors and the GPS receiver. The wearable device may further include a memory storing computer-executable instructions for controlling the at least one processor to: determine that a user of the wearable device has started an exercise; activate the GPS receiver in response to determining that the user has started the exercise; detect a time at which the GPS receiver achieves an initial GPS fix of a location of the wearable device; determine, based on output of the one or more biometric sensors, a first set of user data relating to at least one of distance, direction, and speed of the user during a first time interval between the start of the exercise and the detected time of the initial GPS fix; and back-fill an exercise route of the user during the first time interval based on the first set of user data.

In yet another aspect, there is provided a non-transitory computer readable storage medium having stored thereon instructions that, when executed, cause a processor of a wearable device to: determine that a user of the wearable device has started an exercise; activate a GPS receiver of the wearable device in response to determining that the user has started the exercise; detect a time at which the GPS receiver achieves an initial GPS fix of a location of the wearable device; log, based on output of one or more biometric sensors of the wearable device, a first set of user data relating to at least one of distance, direction, and speed of the user during a first time interval between the start of the exercise and the detected time of the initial GPS fix; and back-fill an exercise route of the user during the first time interval based on the first set of user data.

In still another aspect, there is provided a method of operating a wearable device that includes a geolocation sensor. The method may involve: determining that a user of the wearable device has started an exercise; activating the geolocation sensor in response to determining that the user has started the exercise; obtaining an initial geolocation fix of a location of the wearable device from the geolocation sensor; and retrieving one or more candidate start locations of the exercise from a memory. The method may further involve identifying one of the one or more candidate start locations as a start location of the exercise; and back-filling an exercise route of the user from the location of the initial geolocation fix to the identified start location of the exercise.

DETAILED DESCRIPTION

Figure 1A:
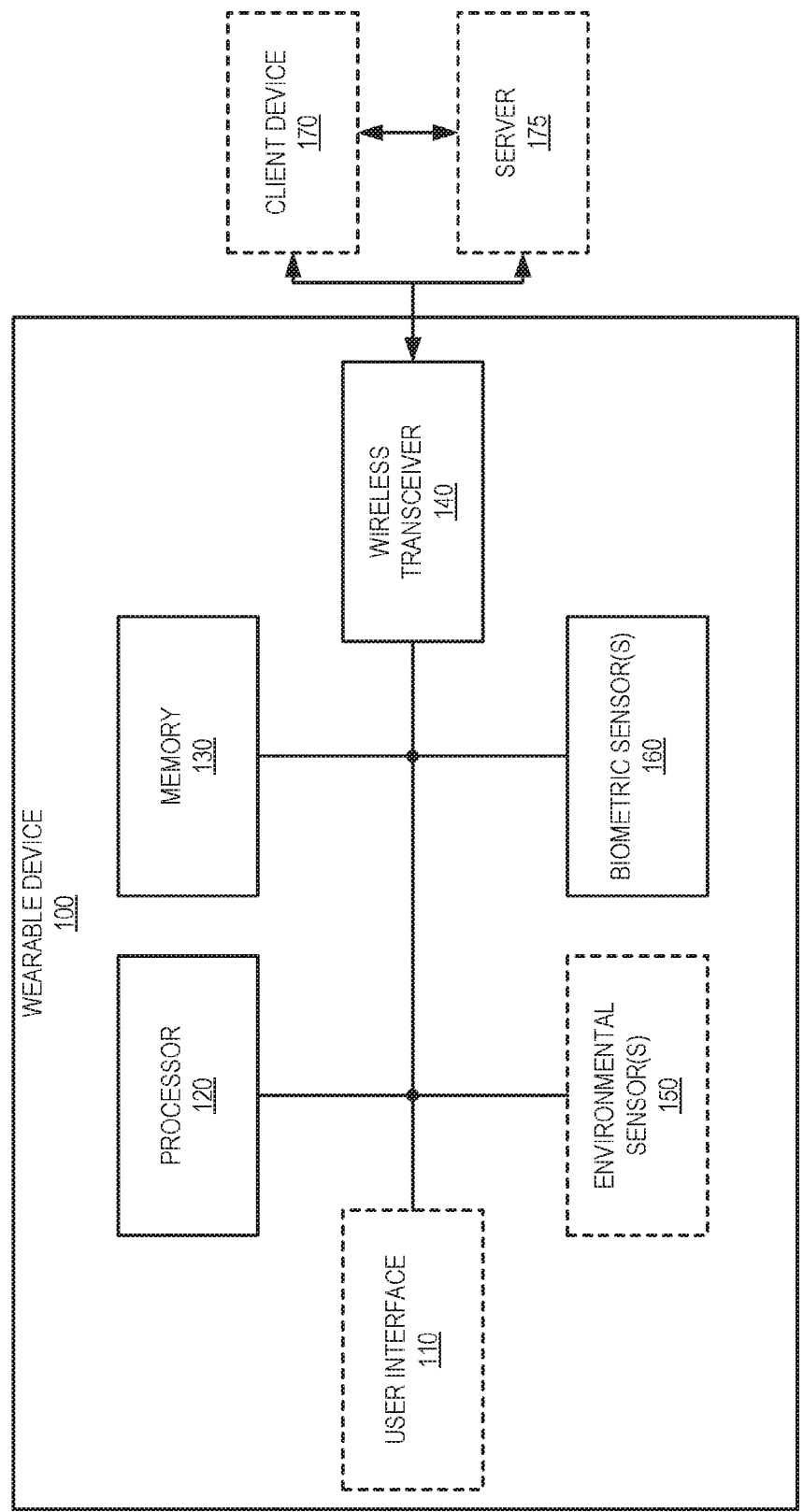
FIG. 1A is a block diagram illustrating certain components of an example wearable device in accordance with aspects of this disclosure.

One of the applications of wearable devices may be the tracking of an exercise performed by a user of a wearable device via at least one biometric sensor. Various algorithms or techniques for tracking exercises have been developed and these algorithms may be specialized based on the type of exercise performed by the user. For example, when the exercise that a user desires to track is an outdoor run, a specialized outdoor run algorithm may be performed based on data received from a motion sensor, a heart rate monitor, and/or a global positioning system (GPS) receiver. However, when the user decides to track an indoor or treadmill run, data from the GPS receiver may not be needed since the user will not be moving a sufficient distance for the GPS receiver data to be useful in tracking the exercise. The different algorithms for tracking various exercises may include, but are not limited to, outdoor running, indoor/treadmill running, outdoor biking, indoor/stationary biking, swimming, hiking, etc. Certain embodiments of this disclosure may also apply to the GPS tracking of other activities, such as driving (e.g., the tracking of geolocation data while driving in a vehicle) or any activity where GPS geolocation data may be tracked.

Although the techniques of this disclosure may be described in connection with the tracking of the geolocation of a wearable device via a GPS receiver, this disclosure is not limited to the use of a GPS receiver or component(s) thereof. Other geolocation tracking techniques that may be used in place of, or in addition to, a GPS receiver may include, for example, tracking location via a wireless wide area network (WWAN) radio circuit/chip or component(s) thereof (e.g., configured for communication via one or more cellular networks), via a wireless local area network (WLAN) radio circuit/chip or component(s) thereof (e.g., configured for one or more standards, such as the IEEE 802.11 (Wi-Fi)), etc.

In related aspects, each of the GPS receiver, the WLAN radio circuit, and the WLAN radio circuit may be referred to as geolocation sensor. One or more geolocation sensors may be implemented as a System-on-Chip (SoC). For example, the SoC may include one or more central processing unit (CPU) cores, a GPS receiver, a WLAN radio circuit, a WWAN radio circuit, and/or other software and hardware to support the wearable device.

In further related aspects, the terms "location" and "geolocation" may be used interchangeably herein. The terms "location" and "geolocation" generally refer to the real-world geographic location of an object, such as a wearable device, which may be determined by one or more of the above-mentioned geolocation tracking techniques.

Geolocation data may be used by certain exercise tracking algorithms to supplement data received from other biometric sensors of a wearable device. For example, during a running exercise, geolocation data that is tracked may be: displayed to the user during/after the exercise; used to calibrate the distance estimations from other biometric sensors of the wearable device; and/or used to determine certain physiological metrics associated with the running exercise (e.g., calories burned). Those skilled in the art will recognize that geolocation data may be used to determine many other physiological metrics associated with an exercise, including but not limited to altitude, heart rate, heart rate variability, speed/pace, etc.

It may be desirable for a wearable device to automatically track an exercise and the associated geolocation for the exercise. For example, a user may forget to input the start of an exercise to the wearable device and/or may not wish to take the time to input the start of the exercise. Accordingly, the wearable device may be able to automatically detect that the user has started an exercise based on the output from biometric sensor(s) of the wearable device. However, certain movements and/or actions performed by a user may be similar to movements during an exercise. For example, a user may run to catch a bus, or run on a treadmill indoors. In these situations, the tracking of geolocation may not be desirable, and thus, turning on or running the GPS sensor (and/or other geolocation sensor(s)) at a high resolution may lead to excess or unnecessary battery usage. Accordingly, certain aspects of the present disclosure are directed to techniques for the accurate detection and identification of exercises for which it is desirable to track geolocation data, as well as the adjusting of a GPS receiver (and/or other geolocation sensor(s)) for the exercises.

In accordance with one illustrative example, GPS receivers typically require an initial GPS fix prior to the tracking of geolocation data. For example, in order to obtain a first positional fix using a GPS receiver (either a GPS receiver that has never been used before or a GPS receiver that has been turned off for a long period of time or that has been moved a large distance while turned off), the GPS receiver may spend a large amount of time, e.g., 12.5 minutes, downloading a GPS almanac from one or more of the GPS satellites within range. The 12.5 minute download duration is a limitation of the GPS satellite transmitter bandwidth (e.g., 50 bits per second). As discussed below, there are certain techniques which may be used to reduce the required time to reach the first positional fix, however, these techniques may require additional energy, thereby consuming battery life of the wearable device and/or still involve some delay before the initial GPS fix. Due to this time required to obtain a first positional fix, if the GPS receiver has not been turned on prior to the start of an exercise, the GPS geolocation data may not be available for an initial time period of the exercise. Accordingly, the GPS geolocation data may begin with geolocation data approximately 12.5 minutes after (or at a time that is well after) the user has started the exercise.

The time to obtain the first positional GPS fix (time-to-first-fix, or TTFF) may be shortened dependent on a number of factors, including the start state of the GPS receiver. A GPS receiver may perform a "hot start," a "warm start," and a "cold start." With a hot start, the GPS receiver may remember or store its last calculated position, which GPS satellites were in view of the receiver, the almanac that was used, and the coordinated universal time (UTC) from the last time it was powered on, and may, using such existing information, have a TTFF on the order of a few seconds, e.g., 1 to 5 seconds. With a warm start, the GPS receiver may remember its last calculated position, almanac used, and UTC, but not which satellites were in view. A GPS receiver performing a warm start may achieve a TTFF on the order of less than a minute. With a cold start, the GPS receiver must re-download the entire almanac from a GPS satellite, which may take on the order of 12-15 minutes. The start state may depend on how far the GPS receiver moved since the last positional fix was obtained, as well as on how long it has been since the most recent positional fix. The almanac data and ephemeris data may be updated periodically to adjust for orbital drift and other factors, so any such data that has been downloaded to a GPS receiver must be re-downloaded if sufficient time has passed. Ephemeris data typically has a shelf life of about 4 hours, and is usually updated every 2 hours; almanac data is typically refreshed every 24 hours.

The lack of initial GPS geolocation data may be particularly pronounced for the automatic tracking of exercises or for exercises where the user does not wait for a GPS fix. When a user manually starts the tracking of an exercise, there may be sufficient time to notify the user that an initial GPS positional fix is not yet available or to obtain the GPS fix between the time the user indicates that they will be performing an exercise and the start of the exercise. However, the automatic tracking of an exercise, e.g., the detection of the user performing an exercise by the wearable device without user interaction, may occur a period of time after the user has started the exercise, and thus, there may not be sufficient time to obtain an initial GPS position fix. This may lead to the loss of positional or geolocation data for a period of time after the start of the exercise. Certain aspects of this disclosure relate to techniques for obtaining location or position data between the start of an exercise and the initial GPS position fix. The user may not wish to wait for the initial GPS fix before starting an exercise. Accordingly, a portion of the exercise may not have associated GPS geolocation data available.

Wearable Device Overview

FIG. 1A is a block diagram illustrating an example wearable device in accordance with aspects of this disclosure. The wearable device 100 may include a processor 120, a memory 130, a wireless transceiver 140, and one or more biometric sensor(s) 160. The wearable device 100 may also optionally include a user interface 110 and one or more environmental sensor(s) 150. The wireless transceiver 140 may be configured to wirelessly communicate with a client device 170 and/or server 175, for example, either directly or when in range of a wireless access point (not illustrated) (e.g., via a personal area network (PAN) such as Bluetooth pairing, via a WLAN, etc.). Each of the memory 130, the wireless transceiver 140, the one or more biometric sensor(s) 160, the user interface 110, and/or the one or more environmental sensor(s) 150 may be in electrical communication with the processor 120.

The memory 130 may store instructions for causing the processor 120 to perform certain actions. For example, the processor 120 may be configured to automatically detect the start of an exercise performed by a user of the wearable device 100 and adjust a GPS receiver based on instructions stored in the memory 130. The processor 120 may receive input from the one or more of the biometric sensor(s) 160 and/or the one or more environmental sensor(s) 150 in order to determine or back-fill a route of the user during a first interval between the start of an exercise and a time at which a GPS receiver achieves an initial fix of the location of the wearable device after the start of the exercise. In some embodiments, the biometric sensors 160 may include one or more of an optical sensor (e.g., a photoplethysmographic (PPG) sensor), an accelerometer, a GPS receiver, and/or other biometric sensor(s). Further information regarding such biometric sensors are described in more detail below (e.g., in connection with FIG. 1B).

The wearable device 100 may collect one or more types of physiological and/or environmental data from the one or more biometric sensor(s) 160, the one or more environmental sensor(s) 150, and/or external devices and communicate or relay such information to other devices (e.g., the client device 170 and/or the server 175), thus permitting the collected data to be viewed, for example, using a web browser or network-based application. For example, while being worn by the user, the wearable device 100 may perform biometric monitoring via calculating and storing the user's step count using the one or more biometric sensor(s) 160. The wearable device 100 may transmit data representative of the user's step count to an account on a web service (e.g., world wide web site fitbit.com), computer, mobile phone, and/or health station where the data may be stored, processed, and/or visualized by the user. The wearable device 100 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 100 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 100 (and/or the client device 170 and/or the server 175) may collect data from the biometric sensor(s) 160 and/or the environmental sensor(s) 150, and may calculate metrics derived from such data. For example, the wearable device 100 (and/or the client device 170 and/or the server 175) may calculate the user's stress or relaxation levels based on a combination of heart rate variability, skin conduction, noise pollution, and/or sleep quality. In another example, the wearable device 100 (and/or the client device 170 and/or the server 175) may determine the efficacy of a medical intervention, for example, medication, based on a combination of data relating to medication intake, sleep, and/or activity. In yet another example, the wearable device 100 (and/or the client device 170 and/or the server 22) may determine the efficacy of an allergy medication based on a combination of data relating to pollen levels, medication intake, sleep and/or activity. These examples are provided for illustration only and are not intended to be limiting or exhaustive.

Figure 1B:
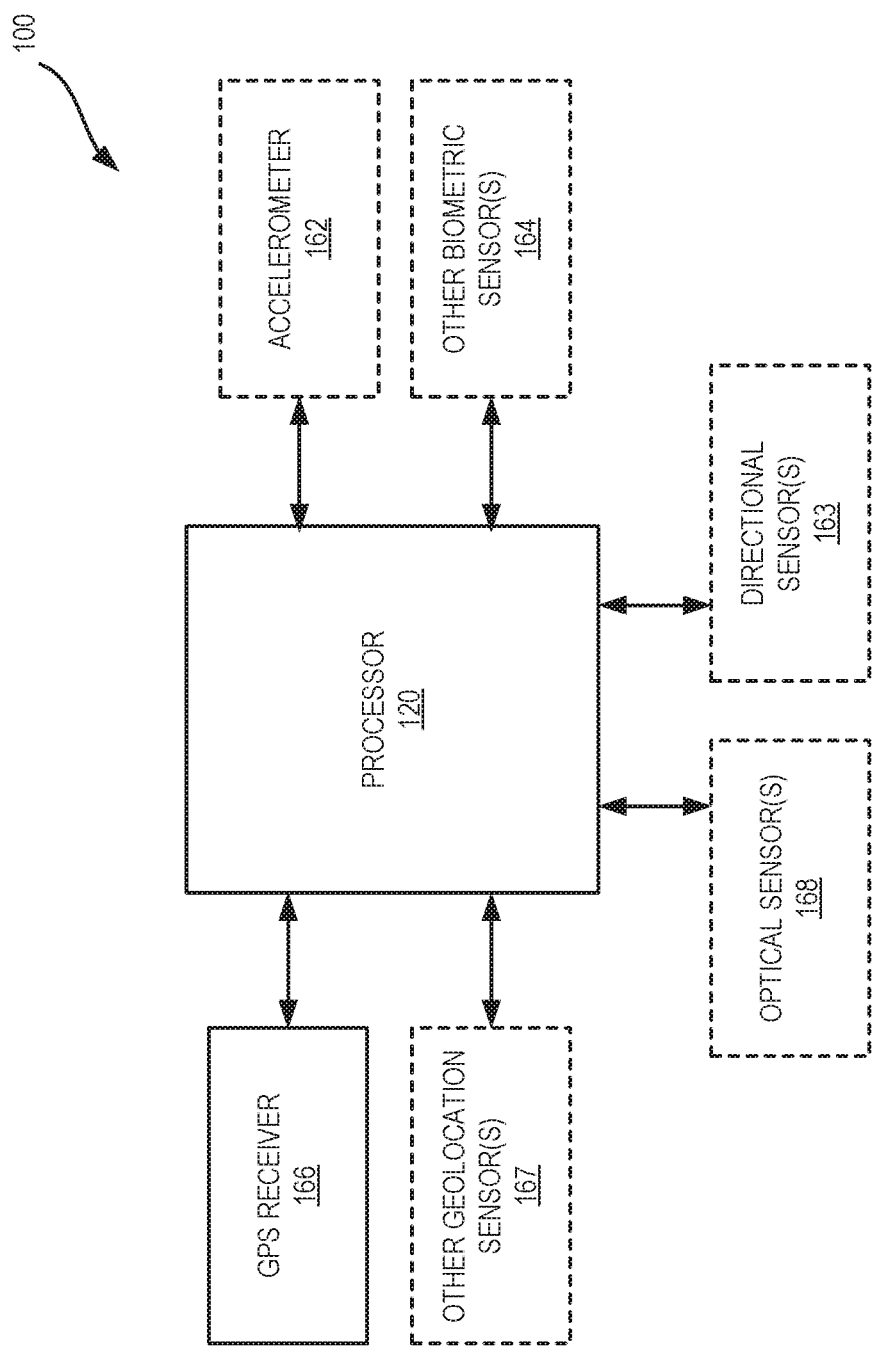
FIG. 1B is a block diagram illustrating example biometric sensors which may be in communication with a processor of a wearable device in accordance with aspects of this disclosure.

FIG. 1B is a block diagram illustrating a number of example biometric sensors that may be in communication with the processor of the wearable device in accordance with aspects of this disclosure. For example, in the embodiment of FIG. 1B, the wearable device 100 may include a GPS receiver 166 which may be used to determine the geolocation of the wearable device 100. The wearable device 100 may further include optional geolocation sensor(s) 167 (e.g., WWAN and/or WLAN radio component(s)), in addition to or in lieu of the GPS receiver 166. The wearable device 100 may further include optional optical sensor(s) 168 (e.g., a PPG sensor), and may optionally include an accelerometer 162 (e.g., a step counter), direction sensor(s) 163, and/or other biometric sensor(s) 164. Examples of the directional sensor(s) include the accelerometer 162, gyroscopes, magnetometers, etc. Each of the biometric sensors illustrated in FIG. 1B is in electrical communication with the processor 120. The processor 120 may use input received from any combination of the GPS receiver 166, the optical sensor(s) 168, the accelerometer 162, and/or the other biometric sensor(s) 164 in detecting the start of an exercise and/or in tracking the exercise. In some embodiments, the GPS receiver 166, the optical sensor(s) 168, the accelerometer 162, and/or the other biometric sensor(s) 164 may correspond to the biometric sensor(s) 160 illustrated in FIG. 1A.

Additionally, in some implementations, the GPS receiver 166 and/or other geolocation sensor(s) 167 may be located in the client device 170 rather than the wearable device 100. In these implementations, the processor 120 may wirelessly communicate with the client device 170 to control and/or receive geolocation data from the GPS receiver 166 and/or the other geolocation sensor(s) 167.

It related aspects, the processor 120 and other component(s) of the wearable device 100 (e.g., shown in FIGS. 1A and 1B) may be implemented as any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure.

In further related aspects, the processor 120 and other component(s) of the wearable device 100 may be implemented as a SoC that may include one or more CPU cores that use one or more reduced instruction set computing (RISC) instruction sets, a GPS receiver 166, a WWAN radio circuit, a WLAN radio circuit, and/or other software and hardware to support the wearable device 100.

Figure 1C:
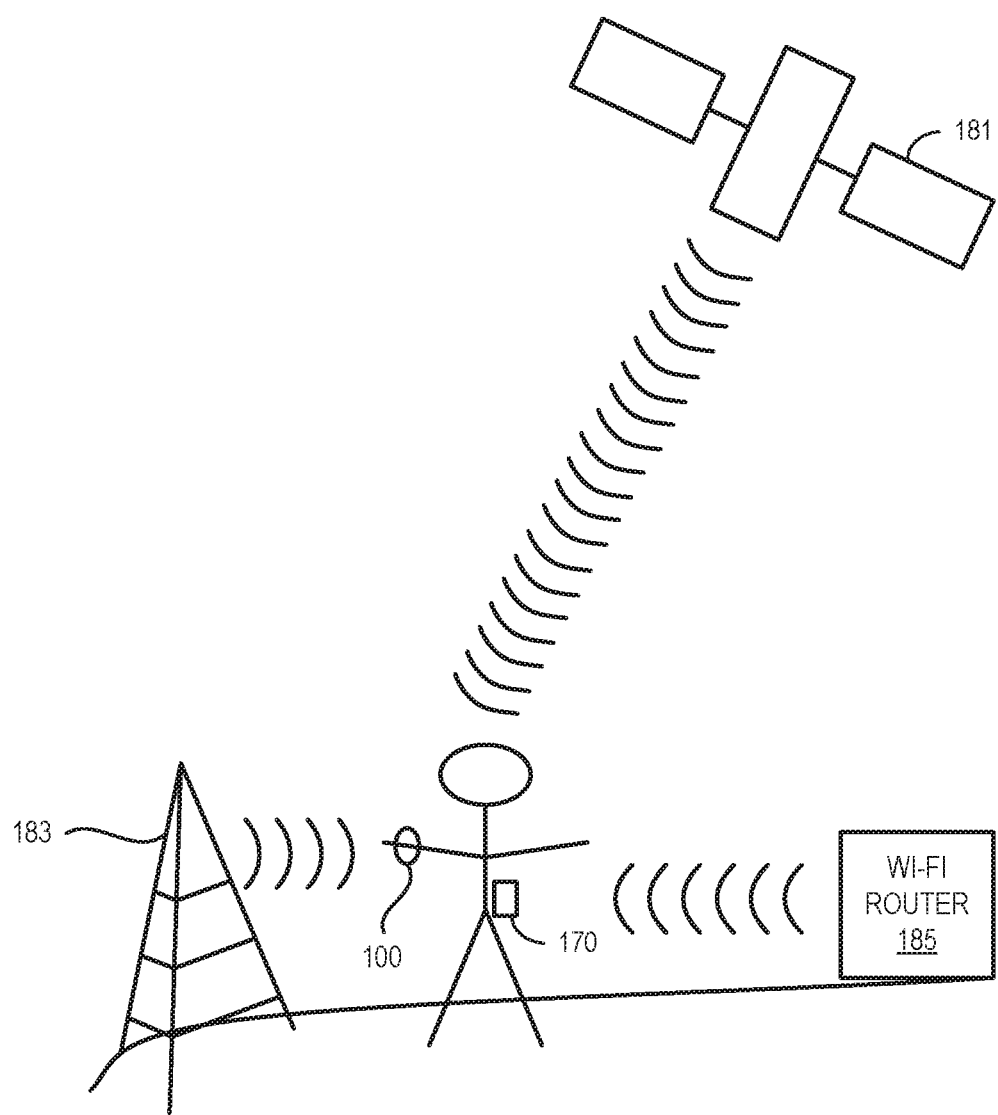
FIG. 1C is an example block diagram illustrating a number of geolocation sensors that may be used in determining the location of the wearable device in accordance with aspects of this disclosure.

FIG. 1C is an example block diagram illustrating geolocation sensor(s) that may be used in determining the location of the wearable device in accordance with aspects of this disclosure. As shown in FIG. 1C, a user is wearing a wearable device 100 and is carrying a client device 170. A given geolocation sensor (e.g., the GPS receiver 166) of the wearable device 100 and/or the client device 170 may receive geolocation data from a GPS satellite 181. Although only one GPS satellite 181 is illustrated in FIG. 1C, the geolocation sensor may receive data from a plurality of GPS satellites at one time, typically three or more GPS satellites.

The geolocation sensor(s) (e.g., WWAN and/or WLAN radio component(s) in the wearable device 100 and/or the client device 170) may also receive geolocation data from a cellular base station 183 and/or a Wi-Fi router 185. Those skilled in the art will recognize that the geolocation sensor(s) may be able to determine the location of the wearable device 100 based on information received from the cellular base station 183 and/or the Wi-Fi router 185. For example, the cellular base station 183 may include geolocation data in the communications with the wearable device 100 and/or the client device 170 or may provide the wearable device 100 and/or the client device 170 with a unique identifier that identifies the cellular base station 183. Thus, a given geolocation sensor may be able to determine the location of the cellular base station 183 based on the unique identifier and retrieve the corresponding location from a memory 130 or from a server 175 (which may be connected to the wearable device 100 and/or the client device 170 via the Internet). The geolocation sensor may also be able to infer the distance of the wearable device 100 from the cellular base station 183 based on the strength of the signal received therefrom. The geolocation sensor may also be able to estimate the location of the wearable device 100 based on triangulation techniques with three or more cellular base stations 183.

The geolocation sensor(s) may also be able to determine the location of the wearable device 100 based on data received from the Wi-Fi router 185. The determination of the location of the wearable device 100 based on the data from the Wi-Fi router 185 may be similar to the techniques used for determining location based on the data received from the cellular base station 183. For example, a given geolocation sensor may receive a unique identifier (e.g., an Internet Protocol (IP) address, Service Set Identifier (SSID), etc.) from the Wi-Fi router which from which the geolocation sensor may look up the location of the Wi-Fi router. Additionally, the geolocation sensor may refine the geolocation data received from the Wi-Fi router based on the strength of the received Wi-Fi signal, which may be related to the distance of the wearable device 100 from the Wi-Fi router.

In related aspects, the processor(s) 120 of the wearable device 100 (and/or the processor(s) on the client device 170 paired with the wearable device 100) may determine the determine the availability and reliability of geolocation data from the GPS receiver 166 and/or the other geolocation sensor(s) 167, and select a subset or portion of the geolocation data to use in determining the geolocation of the wearable device 100. In further related aspects, the processor(s) 120 of the wearable device 100 (and/or the processor(s) on the client device 170) may aggregate the geolocation data from GPS receiver 166 and/or the other geolocation sensor(s) 167, and may determine the geolocation of the wearable device 100 based on the aggregated geolocation data.

Measuring Heart Rate and/or Heart Rate Variability

Figure 1D:
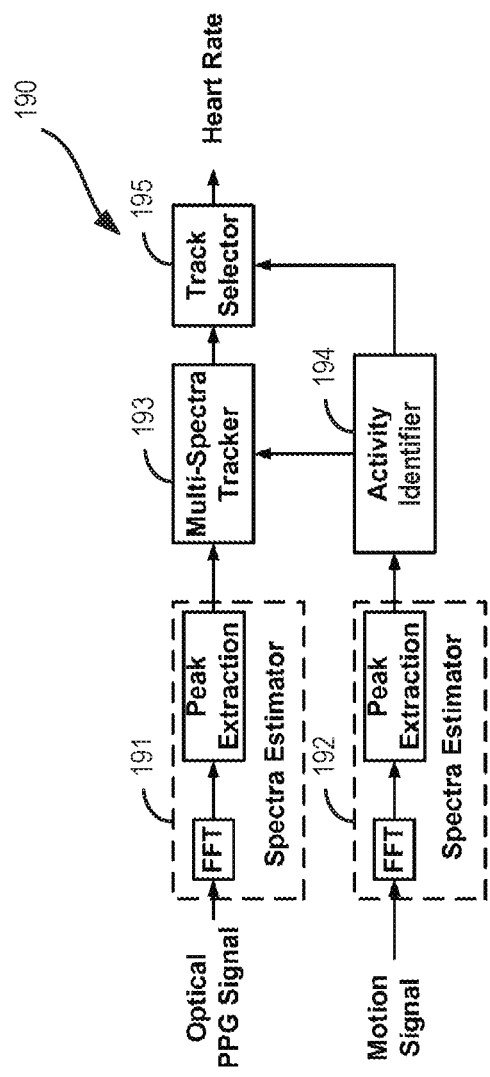
FIG. 1D is an example block diagram of a system used for determining heart rate in accordance with aspects of this disclosure.

FIG. 1D is an example block diagram of a system used for determining heart rate in accordance with aspects of this disclosure. As shown in FIG. 1D, the wearable device 10 may include a system 190 of circuit components for determining the heart rate of the user based on an optical PPG signal (e.g., received from the optical sensor 168) and a motion signature (e.g., received from the accelerometer 162). As used herein, a motion signature may refer to any biometric signature or signal that may be received from and/or based on output data from one or more of the biometric sensor(s) 160 which may be indicative of the activity and/or physiological state of a user of the wearable device 100. The system 190 may be implemented by hardware components and/or in software executed by the processor 120. The system 190 may include first and second spectra estimators 191 and 192, a multi-spectra tracker 193, an activity identifier or discriminator 194, and a track selector 195. Each of the first and second spectra estimators 191 and 192 may include a Fast Fourier Transform (FFT) block and a peak extraction block. In the example of FIG. 1D, the activity identifier 194 may use the peaks extracted from the motion signature to determine the activity that the user is performing (e.g., sedentary, walking, running, sleeping, lying down, sitting, biking, typing, elliptical, weight training, etc.). This determination of the current activity of the user may be used by the multi-spectra tracker 193 and the track selector 195 in extracting the heart rate from the optical PPG signal. Thus, the motion signature in FIG. 1D may be used by the system 190 to determine the current activity of the user. In other embodiments, the processor 120 may use a similar technique to the activity identifier 194 in determining the type of an exercise, as discussed in greater detail below.

The blocks illustrated in FIG. 1D are merely examples of components and/or processing modules that may be performed to supplement a PPG signal with a motion signature to determine heart rate. However, in other implementations, the system 190 may include other blocks or may include input from other biometric sensors of the wearable device 100.

Under certain operating conditions, the heart rate of the user may be measured by counting the number of signal peaks within a time window or by utilizing the fundamental frequency or second harmonic of the signal (e.g., via an FFT). In other cases, such as heart rate data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signature and the output may be used to perform activity discrimination which may be used to assist the multi-spectra tracker 193. For instance, it may be determined that the user was stationary and has begun to move. This information may be used to by the multi-spectra tracker 193 to bias the track continuation toward increasing frequencies. Similarly, the activity identifier 194 may determine that the user has stopped running or is running slower and this information may be used to preferentially bias the track continuation toward decreasing frequencies.

Tracking may be performed by the multi-spectra tracker 193 with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 195 may use the output tracks from the multiple-spectra tracker 193 and estimate the user's heart rate based on the output tracks. The track selector 195 may estimate a probability for each of the tracks that the corresponding track is representative of the user's heart rate. The estimate may be taken as the track having the maximum probability of being representative of the user's heart rate, a sum of the tracks respectively weighted by their probabilities of being representative of the user's the heart rate, etc. The activity identifier 194 may determine a current activity being performed by the user which may be used by the track selector 195 in estimating the user's heart rate. For instance, when the user is sleeping, sitting, lying down, or sedentary, the user's estimated heart rate may be skewed toward heart rates in the 40-80 bpm range. When the user is running, jogging, or doing other vigorous exercise, the user's estimated heart rate may be skewed toward elevated heart rates in the 90-180 bpm range. The activity identifier 194 may determine the user's current activity (e.g., a current exercise) based at least in part on the speed of the user. The user's estimated heart rate may be shifted toward (or wholly obtained by) the fundamental frequency of the selected output track when the user is not moving. The output track that corresponds to the user's heart rate may be selected by the track selector 195 based on criteria that are indicative of changes in activity. For instance, when the user begins to walk from being stationary, the track selector 195 may select the output track that illustrates a shift toward higher frequency based on output received from the activity discriminator 194.

Figure 2:
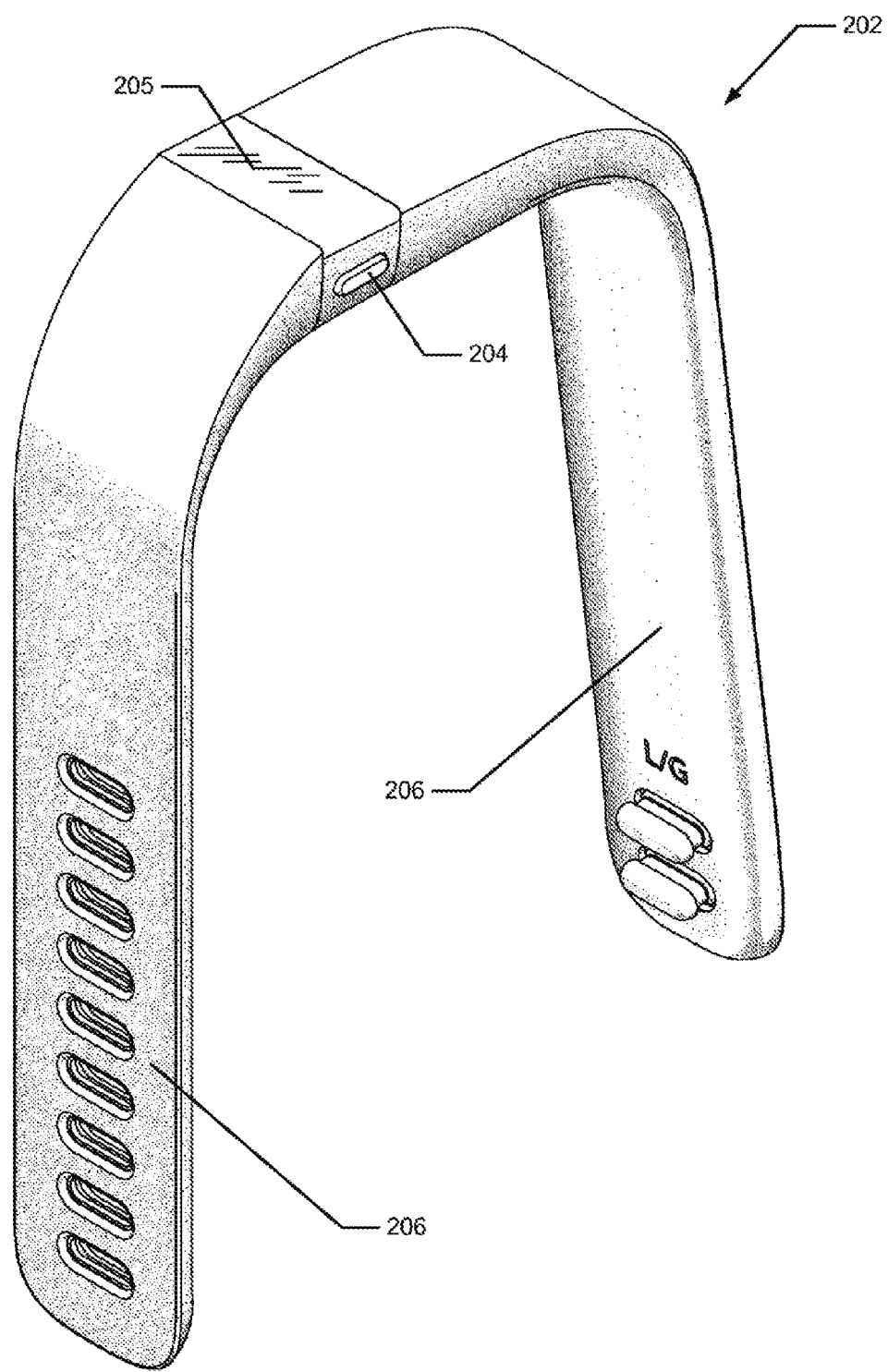
FIG. 2 is an example of a wrist-worn device in accordance with aspects of this disclosure.

The wearable device 100 according to embodiments and implementations described herein may have a shape and/or size adapted for coupling to (e.g., secured to, worn, borne by, etc.) the body or clothing of a user. FIG. 2 shows an example of a wrist-worn wearable device 202 in accordance with aspects of this disclosure. The wrist-worn wearable device 202 may have a display 205, button(s) 204, electronics package (not illustrated), and/or an attachment band 206. The attachment band 206 may be secured to the user through the use of hooks and loops (e.g., Velcro), a clasp, and/or a band having memory of its shape, for example, through the use of a spring metal band.

Figure 3:
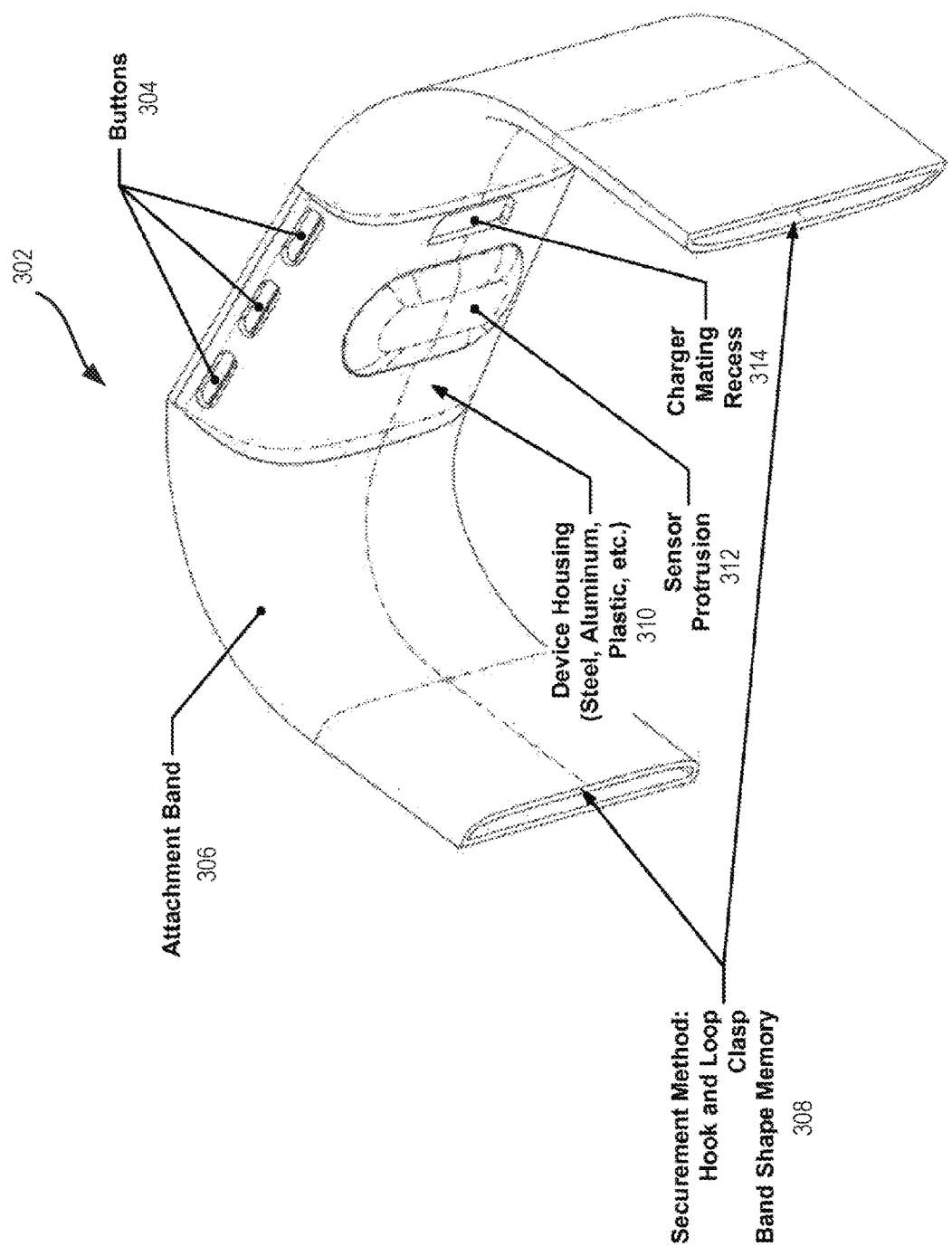
FIG. 3 is a perspective view illustrating another example of a wrist-worn device in accordance with aspects of this disclosure.

FIG. 3 is a perspective view illustrating another example of a wrist-worn device in accordance with aspects of this disclosure. The wrist-worn wearable device 302 of FIG. 3 may include button(s) 304, an attachment band 306, fasteners 308 (e.g., hook and loops, clasps, or band shape memory), a device housing 310, a sensor protrusion 312, and/or a charging/mating recess 314 (e.g., for mating with a charger or data transfer interface of a cable, etc.). In contrast to the wrist-worn wearable device 202 of FIG. 2, in FIG. 3, the wrist-worn wearable device 302 includes the sensor protrusion 312 and the recess 314 for mating with a charger and/or data transmission cable. FIG. 3 also illustrates the device housing 310 which may house internals of the wrist-worn wearable device 302 such as, for example, the processor 120, the GPS receiver 166, the optical sensor(s) 168, and/or the accelerometer 162. The optical sensor(s) 168 may be housed directly below the sensor protrusion 312.

Automatic Detection of Exercise(s)

Certain aspects of this disclosure relate to the automatic tracking of exercises, including the tracking of geolocation data. As described above, one application for a wearable device, such as the wearable device 100, is the tracking of exercises performed by a user of the wearable device 100. While a user may manually start and/or end the tracking of an exercise, which may involve the selection of the type of the exercise to be performed, along with the optional selection of goals such as a target heart rate, distance, exercise time period, etc., the techniques described herein may allow a user to start and/or end an exercise without manual input or interaction with the wearable device 100, and the wearable device 100 may be able to automatically start and/or stop the tracking of the exercise. This may allow the user to skip the input of start and/or end of the exercise and/or the other parameters and still have the exercise be tracked by the wearable device 100. Further, the described techniques may allow a user to have their exercise(s) tracked even when the user forgets to input an indication of the start and/or end of an exercise to the wearable device 100.

The tracking of geolocation data using a GPS receiver (such as GPS receiver 166) may be useful for exercises such as biking and running. The tracking of these exercises may involve the user manually indicating the start of an exercise by pressing a start button of a wearable device 100 or a connected client device 170 and indicating the end of the exercise by pressing a stop button of the wearable or client device 100 or 170. Data logged during this period, such as the data received from the GPS receiver 166 or various biometric sensors 160, may be used by a processor 120 of the wearable device 100 to provide feedback to the user.

Certain aspect of this disclosure relate to the automated detection and logging of data relating to the start and/or end of the exercise without any manual intervention.

Figure 4:
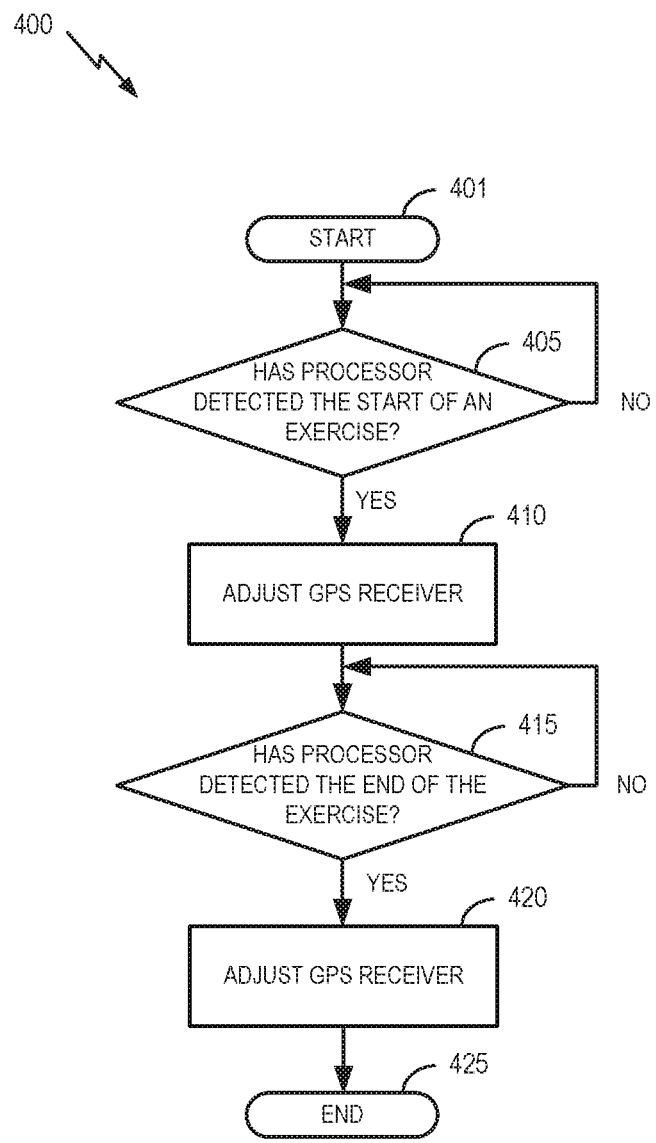
FIG. 4 is a flowchart illustrating a method for the automatic tracking of geolocation data for exercise(s) in accordance with aspects of this disclosure.

FIG. 4 is a flowchart illustrating a method for the automatic tracking of geolocation data for exercise(s) in accordance with aspects of this disclosure. The method 400 may be operable by a wearable device 100, or component(s) thereof, for automatic detection of exercises in accordance with aspects of this disclosure. For example, the steps of method 400 illustrated in FIG. 4 may be performed by a processor 120 of the wearable device 100. In another example, a client device 170 (e.g., a mobile phone) or a server 175 in communication with the wearable device 100 may perform at least some of the steps of the method 400. For convenience, the method 400 is described as performed by the processor 120 of the wearable device 100.

The method 400 starts at block 401. At decision block 405, the processor 120 detects whether or not the start of an exercise has occurred. When the processor 120 detects the start of an exercise, the method 400 proceeds to block 410. When the processor 120 does not detect the start of an exercise, the method 400 remains at block 405, where the processor 120 may routinely, or at defined intervals, determine whether the start of an exercise has been detected.

The processor 120 may detect the start of an exercise based on input received from one or more of the biometric sensor(s) 160. Furthermore, the biometric sensor(s) 160 used in the detection of the start of an exercise may be based on the type of exercise to be detected. For example, a running exercise may be detected based on data received from an accelerometer 162. In one implementation, the processor 120 analyzes step data that is generated based on the data output from the accelerometer 162 to determine whether the user of the wearable device 100 has started a running exercise. Depending on the implementation, the detection of a running exercise may include one or more of: comparing a step rate to a defined step rate threshold, where a step rate greater than the defined step rate threshold is indicative of the user performing a running exercise; comparing the peak accelerations of the accelerometer 162 to a defined peak acceleration threshold, where peak accelerations greater than the defined peak acceleration threshold is indicative of the user performing a running exercise (e.g., user movement characteristic of running may produce larger forces than user movement characteristic of walking or other exercises); and determining whether the data output from the accelerometer 162 matches or is within a threshold range (e.g., defined tolerated difference range) of a motion signature associated with running.

In another implementation, the processor 120 may detect the start of a biking exercise based on data received from the GPS receiver 166. In this implementation, the processor 120 may initially run the GPS receiver 166 at a duty cycle that is less than a threshold duty cycle (e.g., a non-zero resolution that is lower than a threshold resolution). Based on the data output from the GPS receiver 166, the processor 120 may then determine that the user is performing a biking exercise when the location of the GPS receiver 166 is changing at a rate that is greater than a location rate-change threshold. The processor 120 may also base the determination that the user is performing a biking exercise based on a determination of whether data output from one or more of the biometric sensor(s) 160 is within a threshold difference from motion signature(s) associated with biking. In some embodiments, the processor 120 may also detect the start of a running exercise based on data received from the GPS receiver 166, similar to the manner in which data from the GPS receiver 166 may be used to detect the start of a biking exercise as described above. In some embodiments, the processor 120 may detect the start of various exercises (e.g., running, biking, etc.) based on output of a heart rate sensor (e.g., optional optical sensor(s) 168, such as a PPG sensor). For example, data corresponding to an elevated heart rate may indicate that the user has started exercising.

While the detection of running and biking exercises have been given as examples above, this disclosure may also be applied to other forms of exercise (e.g., swimming, hiking, etc.) by applying similar techniques to data received from one or more biometric sensor(s) 160 that are consistent with the types of exercises that may be detected.

After the processor 120 has detected the start of an exercise, the method 400 continues at block 410, where the processor 120, and/or a processor or the client device 170, adjusts the GPS receiver 166 (and/or other geolocation sensor(s) 167). For example, the processor 120 may turn on and/or increase the temporal resolution (hereinafter also referred to simply as a resolution) of the GPS receiver 166. The resolution of the GPS receiver 166 may generally refer to the rate at which distinct GPS location measurements are determined. That is, a higher GPS receiver 166 resolution may include a greater number of geolocation data points per unit of time than a lower GPS receiver 166 resolution. For example, if the GPS receiver 166 is turned off, the processor 120, and/or a processor or the client device 170, may turn on the GPS receiver 166 to initiate the tracking of the location of the GPS receiver 166. In implementations where the GPS receiver 166 is run at a duty cycle that is less than a threshold duty cycle during block 405, at block 410 the processor 120, and/or a processor or the client device 170, may instruct the GPS receiver 166 to increase its resolution (e.g., duty cycle) in order to increase the rate at which geolocation data is output from the GPS receiver 166. Block 410 may also involve the logging of data produced by one or more of the biometric sensor(s) 160 over the course of the exercise.

Block 410 may also involve the processor 120 turning on additional algorithms that process data output from one or more of the biometric sensor(s) 160. The algorithms that are turned on may be based on the type of exercise that the user is performing. For example, when the user is performing a running exercise, the processor 120 may initiate an algorithm for smoothing the pace and/or distance metrics estimated by the processor 120 based on the output of one or more of the biometric sensor(s) 160. In another example, when the user is performing a biking exercise, the processor 120 may initiate algorithms related to the biking exercise, such as an algorithm for smoothing the distance and/or cadence metrics estimated by the processor 120. The algorithms for smoothing pace and/or distance may be turned on at the same time as turning on or increasing the resolution of the GPS receiver 166. In another implementation, the algorithms may relate to at least one of: heart rate estimation, higher resolution heart rate estimation, calorie estimation, distance estimation, pace estimation, and cadence estimation (e.g., where a specific version of each algorithm optimized for a given exercise type may be selected based on the type of the detected exercise).

At decision block 415, the processor 120 detects whether or not the end of the exercise has occurred. When the processor 120 detects the end of the exercise, the method 400 proceeds to block 420. When the processor 120 does not detect the end of the exercise, the method 400 remains at block 410, where the processor 120 may routinely, or at defined intervals, determine whether the end of the exercise has been detected.

The processor 120 may detect the end of the exercise based on input received from the one or more of the biometric sensor(s) 160. For example, the processor 120 may determine that the user has ended the exercise when the output received from the one or more biometric sensor(s) 160 no longer matches motion signatures which are consistent with the type of the exercise. Additionally or alternatively, the processor 120 may determine that the user has ended the exercise when the geolocation data received from the GPS receiver 166 is indicative of the user being substantially stationary (e.g., moving at a rate that is less than expected for the type of the exercise) for a period of time that is greater than a defined time period.

After the processor 120 has detected the end of the exercise, the method 400 may involve the processor 120, and/or a processor or the client device 170, adjusting the GPS receiver. For example, the processor 120 may turn off and/or decrease the resolution of the GPS receiver 166. Accordingly, the GPS receiver 166 may no longer log geolocation data or may log geolocation data at a reduced rate. The method ends at block 425.

Although the detection of running and biking by the processor 120 have been described as independent implementations, in certain implementations the detection processes may be run in parallel or a single detection process may be run which may be used to determine that data received from one or more of the biometric sensor(s) 160 is consistent with the user performing an exercise. The processor 120 may identify the type of the exercise based on whether the data received from one or more of the biometric sensor(s) 160 is within a threshold range of motion signatures associated with the different types of exercises.

Figure 5:
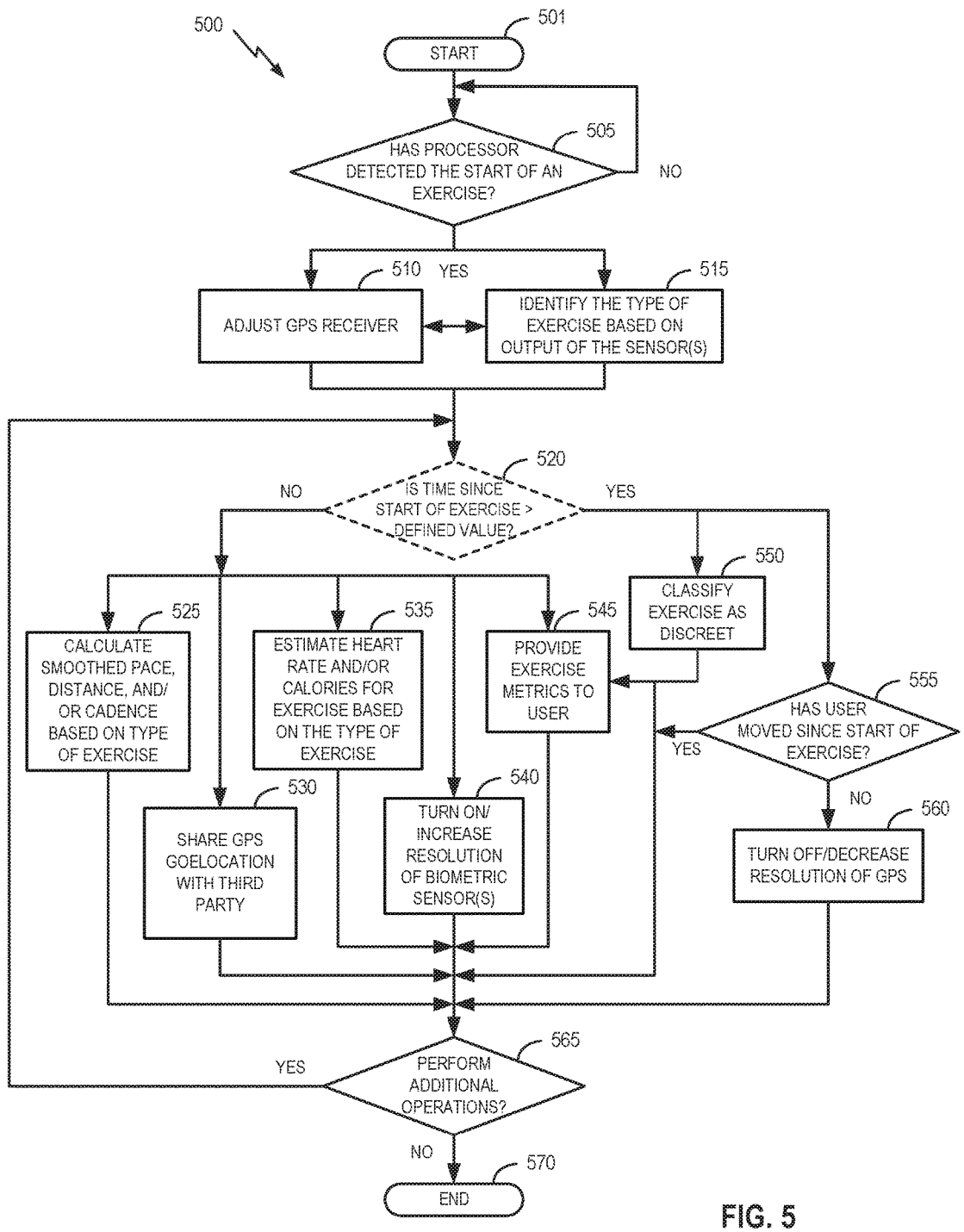
FIG. 5 is a flowchart illustrating another method for the automatic tracking of geolocation data for exercise(s) in accordance with aspects of this disclosure.

Another implementation of the automatic detection of exercises will now be described in connection with FIG. 5. FIG. 5 is a flowchart illustrating another method for the automatic tracking of geolocation data for exercise(s) in accordance with aspects of this disclosure. The method 500 may be operable by a wearable device 100, or component(s) thereof, for automatic detection of exercises in accordance with aspects of this disclosure. For example, the steps of method 500 illustrated in FIG. 5 may be performed by a processor 120 of the wearable device 100. In another example, a client device 170 (e.g., a mobile phone) or a server 175 in communication with the wearable device 100 may perform at least some of the steps of the method 500. For convenience, the method 500 is described as performed by the processor 120 of the wearable device 100.

The method 500 starts at block 501. At decision block 505, the processor 120 detects whether or not the start of an exercise has occurred. When the processor 120 has detected the start of an exercise, the method 500 proceeds to at least one of blocks 510 and 515. When the processor 120 has not detected the start of an exercise, the method 500 remains at decision block 505, where the processor 120 may routinely, or at defined intervals, determine whether the start of an exercise has been detected. The details of how the processor 120 may detect the start of an exercise are described above in connection with FIG. 4, and thus, some of the details regarding the detection of the start of an exercise will not be repeated below.

After the processor 120 has detected the start of an exercise, the method 500 may continue at block 510, where the processor adjusts the GPS receiver 166. For example, the processor 120 may turn on and/or increase the resolution of the GPS receiver 166. For example, if the GPS receiver 166 is turned off, the processor 120 may turn on the GPS receiver to initiate the tracking of the location of the GPS receiver 166. Once the GPS receiver 166 has been turned on or has an increased resolution, the processor 120 may log GPS geolocation data received from the GPS receiver 166. As discussed above, the GPS receiver may be located in the wearable device 100 and/or the client device 170 that is paired with the wearable device 100, and thus, the processor 120 (and/or a processor of the client device 170) may control the logging of data received from the GPS receiver 166 (and/or other geolocation sensor(s) 167) regardless of the location of the GPS receiver 166.

After, prior to, or concurrently with block 510, the method 500 may, at block 515, involve the processor 120 identifying the type of the exercise based on output received from one or more of the biometric sensor(s) 160. For example, the processor 120 may compare the output received from one or more of the biometric sensor(s) 160 to defined sensor data for a plurality of exercise types. For example, the defined sensor data may include motion signatures that are associated with the defined types of exercises. The processor 120 may select the type of exercise for which the associated motion signature is closest to the output received from the one or more biometric sensor(s) 160. In certain implementations, the processor 120 may only select a type of exercise when the output received from the one or more biometric sensor(s) 160 is within a defined tolerance range of the associated motion signature.

In certain implementations, the processor 120 may turn on/increase the resolution of the GPS receiver (e.g., performed at block 510) based on the start of the exercise (e.g., detected at block 505) and the identified type of the exercise (e.g., identified at block 515). In some implementations, different exercise types may require different resolutions. For example, when a user is walking, the user may travel at a lower speed than when the user is biking. As such, the location of the wearable device 100 may not need to be updated at the same resolution for walking as for biking. Thus, the resolution at which the processor 120 sets the GPS receiver may be based on the identified type of the exercise.

At optional decision block 520, the processor 120 may determine whether the time that has elapsed since the start of the exercise is greater than a defined time period. When the time since the start of the exercise is not greater than the defined time period, the method 500 may continue at one or more of blocks 525, 530, 535, 540, and 545. However, in certain implementations, the method 500 may also continue to one of blocks 525, 530, 535, 540, and 545 regardless of the amount of time that has passed since the start of the exercise. When the time since the start of the exercise is greater than the defined time period, the method 500 may continue at one of blocks 550 and 555.

At block 525, the processor 120 may calculate a smoothed pace, distance, and/or cadence based on the identified type of exercise. For example, for a running exercise, the processor 120 may calculate a smoothed pace and distance, while for a biking exercise, the processor 120 may calculate a smoothed distance and cadence (e.g., based on moving averages, Riemannian manifolds, etc.). In order to calculate the smoothed metrics, the processor 120 may initiate an algorithm designed to smooth the metrics calculated from the data received from one or more of the biometric sensor(s) 160 based on the identified type of exercise.

At block 530, the processor 120 may share the GPS geolocation (and or other geolocation data obtained from one or more other geolocation sensors 167) of the wearable device 100 with a third party. For example, the processor 120 may communicate with the third party via a cellular connection of the wireless transceiver 140 and/or a cellular connection of the client device 170 that is paired with the wearable device 100. The shared GPS geolocation may be the most recently determined position of the wearable device 100 and may be shared during the exercise. By sharing the GPS geolocation with a third party (such as a trusted person selected by the user of the wearable device 100), the wearable device 100 may provide a way to monitor the safety of the user of the wearable device 100. The geolocation of the user may be a concern for the user when the user is performing an exercise in an area/region that is unfamiliar to the user or pose safety risks (e.g., routes near cliffs, rock terrain, constructions zones, poorly lit locations, etc.). The user may desire that the third party be aware of the user's geolocation should the user encounter a dangerous situation (e.g., when the user's geolocation metrics may be indicative of the exercise being inadvertently stopped for longer than a defined length of time during the exercise, such as when the user may be injured or otherwise incapacitated). For example, when the output of the GPS receiver 166 is indicative of the user stopping the exercise for more than the defined time period prior to the end of the exercise, the processor 120 may determine that the exercise has been inadvertently stopped. In certain implementations, the user's geolocation and/or a warning message may be sent to the third party when the user's location has not been updated for longer than the defined length of time prior to the end of the exercise.

In some implementations, the accelerometer 162 may be used to determine whether the user has been injured or otherwise incapacitated during the exercise. For example, when the accelerometer 162 detects a sudden stop and/or fall of the user (e.g. the accelerometer data is greater than a defined acceleration threshold), the wearable device 100 may share the geolocation of the wearable device 100 with the third party. The wearable device 100 may prompt the user for confirmation of whether the user has been injured via the user interface 110 in response to the accelerometer data being greater than the defined acceleration threshold. When the user confirms that he/she has been injured or does not respond to the prompt from the wearable device 100 for longer than a predetermined time period, the wearable device 100 may share the geolocation of the wearable device 100 with the third party.

At block 535, the processor 120 may estimate the user's heart rate and/or calories burned during the exercise based on the type of exercise. For example, a calculation used to determine metrics such as the user's heart rate and/or calories burned may be based on data received from one or more of the biometric sensor(s), e.g., the optical sensor(s) 168 and/or the accelerometer 162. However, the algorithms for calculating the heart rate and/or calorie metrics may be optimized for certain types of exercises, and thus, the processor 120 may be able to calculate these metrics more accurately by running algorithms that are selected based on the identified type of exercise (e.g., higher fidelity algorithms that are optimized for that exercise type). For example, a version of a heart rate estimation algorithm optimized for running can be activated and utilized in response to determining that the user is running. As another example, a version of a calorie estimation algorithm optimized for biking can be activated and utilized in response to determining that the user is biking. As another example, a version of a heart rate estimation algorithm optimized for lifting weights can be activated and utilized in response to determining that the user is performing weight lifting repetitions. In certain implementations, the processor 120 may select at least one of the algorithms for calculating the heart rate and/or calorie metrics and increase the fidelity of the selected algorithm based on the identified type of the exercise.

At block 540, the processor 120 may turn on or increase the resolution of one or more of the biometric sensor(s) 160. In one implementation, the processor 120 may increase the resolution of at least one of a heart rate sensor (e.g., the optical sensor 168) and a pulse oxygenation sensor (not illustrated). The higher resolution data (e.g., more frequent measurements) may be used to generate a detailed summary of the exercise which may be displayed to the user (e.g., via the user interface 110, a client device 179, and/or an Internet-connected device). The higher resolution data logged during the exercise may also be stored in a server 175 for later processing and/or display. A subset of the one or more biometric sensor(s) 160 for which the resolution is increased may be based on the identified type of the exercise.

In another implementation, the processor 120 may turn on or increase the resolution of an altimeter (not illustrated). The data logged from the altimeter may be used in conjunction with the GPS receiver data to generate a summary of the changes in elevation of the user during the exercise. This data may be displayed to the user in the form of an elevation profile (e.g., graphed with respect to time or distance) or net elevation gain/loss for the exercise.

At block 545, the processor 120 may display to the user certain metrics related to the exercise and/or indicators or information relating to the metrics (e.g., text and/or graphics). Depending on the implementation, the processor 120 may display the metrics via the user interface 110 or the client device 170. The metrics displayed to the user may include one or more of: speed/pace, distance, heart rate, calories burned, route, floors climbed, repetitions, heart rate zones, duration of exercise, etc. In one embodiment, the metrics are prepared by the processor 120 to be displayed to the user (e.g., automatically and without user input) in response to the detection of the exercise. In certain implementations, the metrics may not be displayed to the user until the processor 120 receives input from the user indicating that the user is ready to view the metrics. The input may include one or more actions performed by the user such as: moving (e.g., rotating and/or lifting) the wearable device 100 to a viewing position; tapping the housing or a button of the wearable device 100; touching a touch screen of the user interface 110; and interacting with the client device 170. The processor 120 may receive the input via one or more of the user interface 110, the accelerometer 162, other biometric sensor(s) 164, and the client device 170. In related aspects, the processor 120 may direct the wearable device 100 to provide to the user an audible message/alert regarding certain metrics related to the exercise.

In one implementation, the processor 120 may prepare the metric for display to the user in response to the processor 120 determining that a confidence metric is indicative of the user performing the exercise. For example, if the user is running for a short period of time that is not consistent with an exercise (e.g., the user is running to catch a bus), the confidence metric calculated by the processor 120 may not be indicative of the user performing the exercise. The confidence metric may be indicative of the user performing the exercise when the confidence metric is greater than a confidence threshold. The confidence metric may be determined by the processor 120 based on one or more of the duration, speed, pace, and cadence of the detected exercise. The confidence metric may be an estimation of the confidence that the detected exercise is intended by the user to be tracked by the wearable device 100. In certain embodiments, the processor 120 may not display exercise metrics to the user. For example, the processor 120 may not alter the display of the user interface 110 except for the addition of a GPS icon indicating that the GPS receiver 166 is active and that geolocation data is being logged. In some embodiments, the logged location data may be used for safety purposes and as a factor for automatically identifying certain activities based on the logged location (e.g., weight lifting at a gym, various exercises at bootcamp, swimming at a pool, etc.).

At block 550, the processor 120 may classify the exercise as discreet in response to the time period since the start of the exercise being greater than a defined time period (e.g., the defined time period used in decision block 520). In one implementation, the defined time period may be 10 minutes. The processor 120 may delay displaying metrics regarding the exercise to the user (e.g., block 545) until the exercise has been classified as discreet. Once the processor 120 has determined the exercise to be a discreet exercise, the processor 120 may select an exercise metric to be displayed to the user. The exercise metric may be one or more of a pace, distance, heart rate, calories burned, route, etc. In one implementation, the method 500 proceeds from block 550 to block 545, where the processor 120 may inform the user that the exercise has been classified as discreet by providing at least one of visual, audio, and haptic feedback to the user relating to the type of the exercise. In one implementation, the processor 120 may provide the feedback to the user via determining or selecting an exercise-related application to be run on the wearable device based on the type of the exercise. The processor 120 may launch the selected exercise-related application. For example, the exercise-related application may be selected from among: a running exercise tracking application, a cycling exercise tracking application, etc.

Additionally, once the exercise has been classified as discreet, the processor 120 may upload data related to the exercise to a server 175 to be displayed to the user at a later time, for example, via a web-interface (e.g., a browser) or mobile dashboard on a mobile device. The data related to the exercise may include geolocation data logged from the GPS receiver 166. The data logged from the GPS receiver 166 may be used by one or more of the processor 120, the client device 170, and the server 175 to calculate one or more metrics or provide other exercise-related information associated with the exercise, such as, for example, route mapping, distance travelled, time elapsed, pace and/or speed of the user, absolute and/or change in elevation, calories burned, training/exercise effort, real-time coaching, duration of exercise, higher resolution heart rate data, heart rate zone distributions, music play control, etc.

At decision block 555, the processor 120 may determine whether the user has moved since the detected start of the exercise. In one implementation, the processor 120 may determine that the user has moved when the distance between a current GPS geolocation and the GPS geolocation of the initial GPS fix or an estimated geolocation of the user at the start of the exercise is greater than a distance threshold. For example, when the distance travelled by the user is less than the distance threshold (e.g., the geolocation of the wearable device 100 has not changed after the initial GPS fix), the processor 120 may determine that the user is performing a stationary exercise, such as a treadmill run or a stationary biking exercise. Accordingly, when the distance travelled by the user is less than the distance threshold, the method may proceed to block 560 at which the processor 120 turns off or decreases the resolution of the GPS receiver 166.

In another implementation, the processor 120 may determine that the user has moved in response to detecting that the geolocation of the wearable device changing at a rate that is greater than a speed threshold. Thus, the method 500 may proceed to block 560 in response to the rate of the change in geolocation of the wearable device 100 being greater than the speed threshold. In one example, decision block 555 may be performed prior to or concurrently with the identification of the type of the exercise in block 515. For example, the processor 120 may identify that the type of the exercise is a non-stationary cycling-type exercise in response to (i) determining that the geolocation of the wearable device 100 is changing at the rate greater than the speed threshold and/or (ii) determining that the output of the one or more biometric sensors is within at least one threshold range of a motion signature of a cycling-type exercise.

Depending on the implementation, the defined time period since the start of the exercise used for the determination in decision block 520 may be different for the classification of the exercise as discreet (e.g., at block 550) than for the determination of whether the user has move since the start of the exercise (e.g., at decision block 555). For example, the defined time period for the method 500 proceeding to decision block 555 may be less than the defined time period for proceeding to block 550.

At decision block 565, the processor 120 may determine whether to perform additional operations. The method 500 may return to decision block 520 when the processor 120 determines to perform additional operations and may proceed to block 570 when the processor 120 has completed performing operations. The method 500 ends at block 570.

In some embodiments, the processor 120 may provide an on-device smart interaction (e.g., via a user interface of the wearable device 100 or client device 170) that enables the user to confirm that they are indeed exercising, or to specify that they are not exercising.

In some embodiments, the processor 120 may communicate with the user's smartphone and other sensors (foot pod, weight pod, etc.) in order to obtain further data (e.g., accelerometer data from the user's smartphone) to better identify and track the appropriate data for various exercise types.

In some embodiments, after the processor 120 automatically determines that the user is exercising, the processor 120 may share a live status and/or general location associated with the user's exercise activity (e.g., "John Smith is running in Lincoln Park") via the user's social graph and/or the user's connections on an online social networking service (e.g., the Fitbit social graph, Facebook, LinkedIn, Twitter, Instagram, etc.). This may be beneficial for both safety reasons and social reasons.

In some embodiments, after the processor 120 automatically determines that the user is exercising, the processor 120 may publish the exercise and exercise details into an exercise challenge (e.g., Fitbit Challenge) that the user is participating in.

In some embodiments, after the processor 120 automatically determines that the user is exercising, the processor 120 may track the user's exercise progress against an exercise goal (e.g., an exercise goal based on exercise frequency per week, or exercise duration per week, or exercise distance per week, or time in heart rate zone per week, or calories burned per week, etc.). All or a subset of the weekly exercise goal metrics could be updated based on the user's tracked exercise progress for all exercises in aggregate, or against specific exercises that the user has specified (e.g., via a user interface of the wearable device 100 or client device 170). For example, a triathlete could track progress against weekly goals for running, biking, and swimming.

In some embodiments, after the processor 120 automatically determines that the user is exercising, the processor 120 may track the user's exercise progress against a training plan. This feature would be for users who have specified their intention (e.g., via a user interface of the wearable device 100 or client device 170) to participate in a training plan that exists within the Fitbit user experience.

In some embodiments, after the processor 120 automatically determines that the user is exercising, the processor 120 may (once the exercise is completed or mid-exercise) trigger achievement alerts for display on the wearable device 100 regarding exercise goals met or personal exercise achievements earned (e.g., "Congrats, you have exercised 3 of 5 days this week!").

In some embodiments, after the processor 120 automatically determines that the user is exercising, the processor 120 may trigger real-time coaching for the user via the user interface of the wearable device 100 (e.g., based on the type of exercise). This feature may be triggered for specific exercises for users who have specified (e.g., via a user interface of the wearable device 100 or client device 170) that they would like to receive coaching for specific exercises.

In some embodiments, after the processor 120 automatically determines that the user is exercising, the processor 120 may turn on music from a Bluetooth connected headset or mobile phone connected via a network to the wearable device 100. The processor 120 may stop the music when the processor 120 automatically detects the end of the exercise.

In some embodiments, after the processor 120 automatically determines that the user is exercising, the processor 120 may play music (e.g., on the wearable device 100, a mobile phone connected via a network to the wearable device 100, or other music/media system connected via a network to the wearable device 100 and/or the mobile phone) based on the type of the exercise or based on the detected current location of the user. Examples include a playlist for gyms, a playlist for bootcamp, a playlist for the track, etc.

In some embodiments, once a user starts exercising, there may be some lag before the exercise is automatically detected (and the appropriate exercise-related algorithms are activated). During this period, exercise relevant data such as high resolution heart rate data and accurate calorie burn data can be estimated by using all day activity data logging (e.g., heart rate data and calorie burn data collected on the current day but before the user started exercising).

Back-Filling of Exercise Route(s)

Certain aspects of this disclosure relate to the back-filling of exercise routes that may not otherwise include complete geolocation data from the start of the exercise. As described above, a user of a wearable device 100 may start or initiate an exercise prior to a GPS receiver 166 (included in the wearable device 100 or the client device 170 that is paired with the wearable device 100) obtaining a GPS fix. For example, the user may select a "quick start" exercise, including the manual start of an exercise prior to obtaining a GPS fix. In another example, the user may start an exercise without manually inputting an indication of the start of the exercise. In this situation, the wearable device 100 may automatically detect the start of the exercise and turn on or increase the resolution of a GPS receiver 166, as discussed above. Accordingly, in certain circumstances, the user may start an exercise before the GPS receiver 166 is able to get a fix of the geolocation of the user.

When the user has started an exercise without a GPS fix, the GPS receiver 166 may obtain a GPS fix at a point in time after the start of the exercise. Thus, GPS receiver 166 may be able to log geolocation data for a portion of the exercise after the initial GPS fix, but geolocation data related to an initial period of the exercise before the GPS fix may not be available. As such, certain aspects of this disclosure relate to the estimation of a route of the exercise prior to an initial GPS fix such that a route of substantially the entire exercise may be stored and/or displayed to the user. For example, the visualization of outdoor exercises, such as, for example, running or biking, may be provided to a user via the display of an exercise route on the wearable device or another device such as, for example, a connected mobile device or a computer. Of course, those skilled in the art would realize that similar delays in an initial geolocation fix may be present in other geolocation sensor(s) 167, and thus, the user may start an exercise prior to the a geolocation sensor obtaining an initial geolocation fix.

Figure 6:
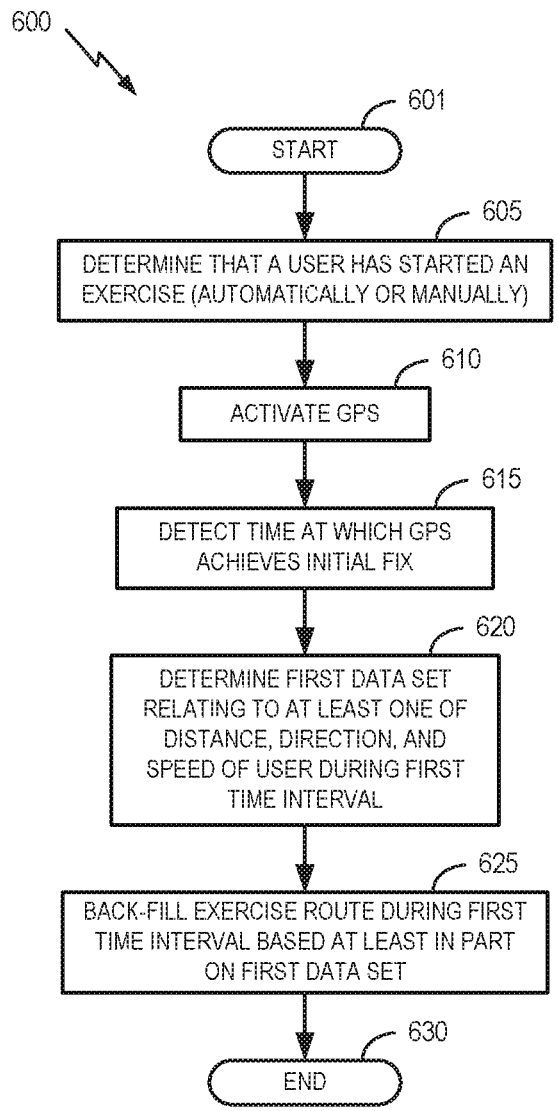
FIG. 6 is a flowchart illustrating a method for the back-filling of exercise route(s) in accordance with aspects of this disclosure.

FIG. 6 is a flowchart illustrating a method for the back-filling of exercise routes in accordance with aspects of this disclosure. The method 600 may be operable by a wearable device 100, or component(s) thereof, for automatic detection of exercises in accordance with aspects of this disclosure. For example, the steps of method 600 illustrated in FIG. 6 may be performed by a processor 120 of the wearable device 100. In another example, a client device 170 (e.g., a mobile phone) or a server 175 in communication with the wearable device 100 may perform at least some of the steps of the method 600. For convenience, the method 600 is described as performed by the processor 120 of the wearable device 100.

The method 600 starts at block 601. At block 605, the processor 120 determines that a user of the wearable device 100 has started an exercise. This determination may be performed manually (e.g., the user inputs an indication of the start of an exercise via, for example, a quick start input) or automatically (e.g., the wearable device 100 automatically detects the start of the exercise based on data received from biometric sensor(s) 160 as described above with reference to FIGS. 4 and 5).

At block 610, the processor 120 activates the GPS receiver 166 (and/or the other geolocation sensor(s) 167). The GPS receiver 166 may take a period of time in order to obtain an initial GPS fix. As discussed above, the amount of time required for the GPS receiver 166 to obtain the initial GPS fix may vary depending on whether the GPS receiver 166 was inactive (e.g., turned off) or running at a low resolution. At block 615, the processor detects the time at which the GPS receiver 166 achieves an initial GPS fix. At block 620, the processor determines a first data set relating to at least one of the distance, direction, and speed of the user during a first time interval. The first time interval may be the time interval between the start of the exercise and the initial GPS fix. Depending on the implementation, the processor 120 may perform block 620 prior to or concurrently with blocks 610 and/or 615.

At block 625, the processor 120 may back-fill the exercise route during the first time interval based at least in part on the first data set. The back-filling of the exercise route may include, for example, estimating the location of the user at various points in time during the first time interval based on one or more of the determined distance, direction, and speed of the user during the first time interval. The method 600 ends at block 630.

Figure 7:
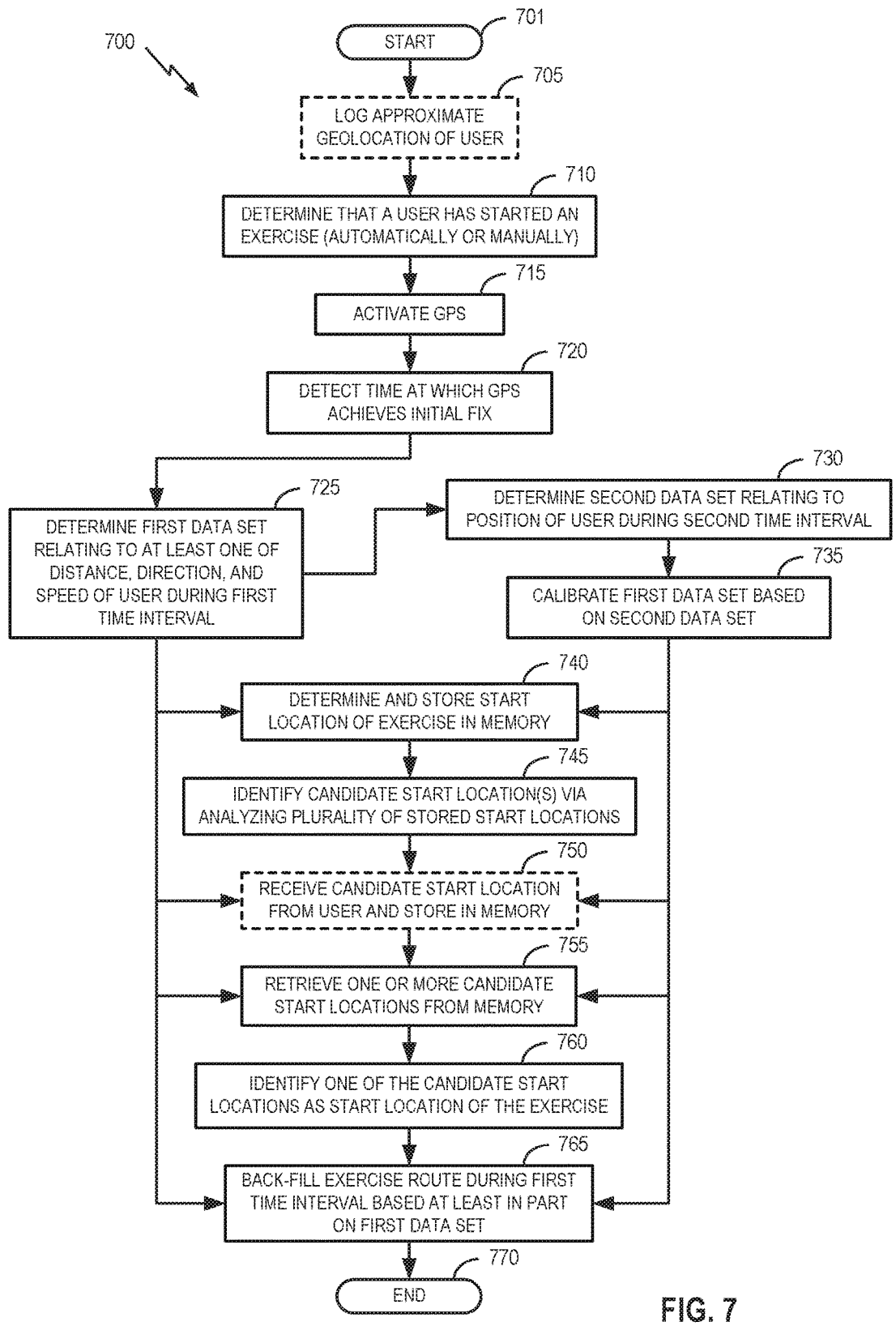
FIG. 7 is a flowchart illustrating another method for the back-filling of exercise route(s) in accordance with aspects of this disclosure.

Another implementation of the back-filling of exercise routes is illustrated in FIG. 7. FIG. 7 is a flowchart illustrating another method for the back-filling of exercise routes in accordance with aspects of this disclosure. The method 700 may be operable by a wearable device 100, or component(s) thereof, for automatic detection of exercises in accordance with aspects of this disclosure. For example, the steps of method 700 illustrated in FIG. 7 may be performed by a processor 120 of the wearable device 100. In another example, a client device 170 (e.g., a mobile phone) or a server 175 in communication with the wearable device 100 may perform at least some of the steps of the method 700. For convenience, the method 700 is described as performed by the processor 120 of the wearable device 100.

The method 700 begins at block 701. At block 705, the processor 120 may optionally log an approximate location of the user. For example, the processor 120 may log geolocation data received from the GPS receiver 166 at a low frequency (e.g., a frequency lower than an exercise frequency used to log GPS geolocation data during an exercise). In the alternative, or in addition, the processor 120 may log geolocation data received from the other geolocation sensor(s) 167 (e.g., WWAN and/or WLAN radio component(s) in the wearable device 100 and/or the client device 170). The logged geolocation data may be used by the GPS receiver 166 to reduce the time required to obtain a first GPS fix. The processor 120, and/or a processor included in the GPS receiver 166, may be able to achieve a quicker GPS fix by having location information of the wearable device 100 estimated from the logged geolocation data. For example, GPS fix may be determined by searching a "search space" until the location of the GPS receiver 166 is determined. The location of the GPS receiver 166 may be estimated based on the logged geolocation data. The processor 120, and/or a processor included in the GPS receiver 166, may use the estimated location to reduce the search space, thereby reducing the amount of time to achieve the GPS fix. The logging of GPS data described in connection with FIG. 7 may also be used in combination with other implementations, e.g., the implementation of FIG. 5, in order to reduce the time to an initial GPS fix.

At block 710, the processor 120 determines that a user of the wearable device 100 has started an exercise. This determination may be performed manually (e.g., the user inputs an indication of the start of an exercise via, for example, a quick start input) or automatically (e.g., the wearable device 100 automatically detects the start of the exercise based on data received from biometric sensor(s) 160). At block 715, the processor 120 activates the GPS receiver 166. The activation of the GPS receiver 166 may include turning on the GPS receiver 166 or increasing the resolution of the GPS receiver 166. The GPS receiver 166 may take a period of time in order to obtain an initial GPS fix. As discussed above, the amount of time required for the GPS receiver 166 to obtain the initial GPS fix may vary depending on whether the GPS receiver 166 was inactive (e.g., turned off) or running at a low resolution. At block 720, the processor detects the time at which the GPS receiver 166 achieves an initial GPS fix.

At block 725, the processor 120 determines a first data set (also referred to herein as a first set of user data) relating to at least one of the distance, direction, and speed of the user during a first time interval. The first time interval may be the time interval between the start of the exercise and the initial GPS fix. Depending on the implementation, the processor 120 may perform block 725 prior to or concurrently with blocks 715 and/or 720. In certain implementations, the processor 120 may log data from one or more biometric sensor(s) 160 from which the first data may be determined. In one implementation, the logging of the first set of user data may include determining one or more direction vectors representative of the user's movement during the first time interval based on output of the one or more biometric sensor(s) 160, such as one or more direction sensors 163 (e.g., gyroscope, magnetometer, etc.). The direction vectors may be indicative of the exercise route during the first time interval.

For example, after block 725, the method 700 may then proceed to one of blocks 730, 740, 750, 755, and 765. At block 730, the processor 120 determines a second set of data relating to the position of the user during a second time interval. The second time interval may begin after the time at which the GPS receiver 166 obtains the initial GPS fix. The second set of data may be geolocation data received from the GPS receiver 166. In certain implementations, the second set of data may be logged based on position data received from the GPS receiver 166 during the second time interval.

In certain implementations, a first set of direction vectors may be determined during the first time interval and a second set of direction vectors may be determined during the second time interval. The second direction vectors may be used by the processor 120 in determining the first direction vectors. For example, the second direction vectors may indicate that the user performed the exercise in a substantially straight line. In this case, the processor 120 may determine that the user did not make any substantial changes in direction during the first time period based on the determination that the user performed the exercise in a substantially straight line during the second time period. The processor 120 may further determine that the user changed the direction of the route during the first time period in response to the output of the one or more biometric sensor(s) 160 being indicative of a change in direction with a corresponding confidence level that is greater than a threshold confidence level. Similarly, if the processor 120 determines that the second direction vectors are consistent with the user performing the exercise in a loop, the processor 120 may supplement the first direction vectors such that the first direction vectors are consistent with the loop identified by the second direction vectors.

At block 735, the processor 120 may calibrate the first set of data based on the second set of data. For example, the first set of data may include data that is estimated based on output receiver from the accelerometer 162, the optical sensor(s) 168, and/or the other biometric sensor(s) 164. Accordingly, the first set of data may include indirect estimations of the distance, direction, and speed of the user. In the alternative, or in addition, the first set of user data may include one or more of step count, step rate, stride length, cadence, and a distance-to-cadence ratio for the user. For example, for a running exercise, distance may be estimated based on a step count determined from data received from the accelerometer 162. For example, the distance estimation may be based on a stride length of the user multiplied by the determined step count. In some embodiment, the stride length may be input by a user of the wearable device 100, or may be calculated based on a height and/or weight input by the user of the wearable device 100 in conjunction with one or more stride length algorithms and/or formulas, or may be determined based on demographic information corresponding to a user of the wearable device 100, and so on. However, a user's stride length may vary based on factors such as the user's energy level, the grade or quality of the terrain, etc. Accordingly, the estimated distance may vary based on the difference between the estimated stride length and the user's actual stride length. In one implementation, the stride length of the user may be calibrated based on the second set of data (e.g., the geolocation data received from the GPS receiver 166 may indicate a given distance traversed by the user, and the given distance may be divided by a number of detected steps taken to traverse the given distance, to thereby produce the calibrated stride length). Since the stride length calibrated based on the GPS geolocation data may be more accurate than the initial estimated stride length, by calibrating the stride length, the estimated distance during the first time period may be improved. Similar calibrations for other measurement data during the first time period may also be performed.

For example, after block 735, the method 700 may proceed to one of blocks 740, 750, 755, and 765. At block 740, the processor 120 determines and stores a start location of the exercise in the memory 130. For example, when time of the initial GPS fix is substantially the same as the time at which the user has started an exercise (e.g., within a threshold time difference), the processor 120 may determine the location of the start of the exercise as the location of the initial GPS fix. The processor 120 may store the start location in the memory 130 as a potential start location for future exercises.

At block 745, the processor may analyze a plurality of previously stored start locations to identify candidate start location(s) for future exercises. For example, when a plurality of stored start locations are clustered (e.g., within a threshold distance from each other), the user may have a history of starting exercises at the clustered start location. The processor 120 or the server may refine the stored start locations via clustering the stored start locations to identify locations at which the user has started exercises a plurality of times. In one implementation, clustering of the start locations may include a hierarchical clustering method to group nearby starting locations. One exemplary hierarchical clustering method is a bottom up agglomerative clustering, which computes the closest two start locations and merges the two closest start locations together by replacing the two closest start locations with, e.g., their mid-point start location. This bottom up agglomerative clustering of the two closest start locations may continue until each of the stored start locations is spaced apart from the closest neighboring start location by more than a threshold distance. Each of the final start locations may represent a group of candidate start locations. Accordingly, the processor 120 may identify a start location that represents the clustered start locations as a candidate start location for the back-filling of exercises.

At block 750, the processor 120 may optionally receive candidate start locations from a user and store the candidate start locations in the memory 130. For example, the processor 120 may prompt the user to accept or decline the candidate start location identified in step 745 for use as a candidate start location for back-filling of exercise route(s). In another implementation, the user may manually select locations as candidate start locations for exercise route back-filling (e.g., via a user interface of the wearable device 100 or client device 170). The manual selection of locations as candidate start locations may be performed prior to the start of method 700 (e.g., block 750 may be performed prior to block 705) when the user is not performing an exercise.

At block 755, the processor 120 may retrieve one or more candidate start locations from the memory 130. At block 760, the processor 120 may identify one of the candidate start locations as a start location of the exercise. For example, the processor 120 may determine that one of the candidate start locations is within a defined distance from the location of the initial GPS fix. The processor 120 may also select one of the candidate start locations based on the first data set. For example, when the first data set is indicative of a distance and direction of the exercise prior to the initial GPS fix, the processor 120 may estimate a start location of the exercise based on the first set of user data and determine that one of the candidate start locations that is within a defined distance from the estimated start location. The processor 120 may select the candidate start location that is within a defined distance from the estimated start location as a start location of the exercise.

At block 765, the processor 120 may back-fill the exercise route during the first time interval based at least in part on the first data set. When a candidate start location has not been identified, the processor 120 may back-fill the route based on the first data set without a predetermined start location. However, when a candidate start location has been identified as the start location of the exercise, the processor 120 may back-fill the route from the initial location of the GPS fix to the start location identified in block 760. The processor 120 may reconstruct the exercise route based on an estimation of the location of the user at various points in time during the first time interval. The distance, direction, and/or speed of the user during the first time interval may be indicative of an approximate location of the user during the first time interval. Further, the back-filling of the exercise route may be further based on the second set of user data (e.g., determined and/or logged at block 730) (e.g., via calibrating the first set of user data based on the second set of user data, via aggregating the first and second sets of user data and back-filling the exercise route based on the aggregated set of user data, and/or via a combination of calibrating and user data aggregation). The method ends at block 770.

In addition to the back-filling of the route, the processor 120 may also use the identified start location to improve estimates of other metrics during the first time interval. For example, distance, speed, and route map estimate may be more accurately calculated by the processor 120 once the start location has been identified since the boundaries of the exercise route can be identified. Thus, the user may be able to view more accurate metrics associated with the exercise in "real-time" during the exercise rather than waiting for updated metrics to be calculated by a client device 170 or server 175 after the exercise have been completed and the user has manually correct the route of the exercise.

In some implementations, the back-filled route data may also be used by the processor 120 to supplement and/or verify biometric data received from the biometric sensor(s) 160. For example, the back-filled route information may indicate that the user has travelled over a hill during the exercise. The processor 120 may be able to retrieve the elevation gains and/or losses expected for the route taken by the user from a map database. This elevation information may be used by the processor 120 to verify and/or supplement the data received from an altimeter. Accordingly, the processor 120 may be able to use additional geolocation data associated with the back-filled route in order to supplement and/or verify the data received from other biometric sensor(s) 160.

Certain aspects of the techniques for automatic detection of exercises may be employed for the back-filling of GPS exercise routes, and vice-versa. For example, the type of the exercise determined in block 515 in FIG. 5 may be used in certain implementations of the exercise route back-filling techniques.

As discussed above, the type of the exercise may be identified based on comparing the output of one or more biometric sensor(s) to define sensor data for a plurality of exercise types. The identified type of exercise may be used by the processor 120 to determine a rate of periodic movement (e.g., the frequency at which certain metrics associated with a specific exercise are repeated) of the exercise during the first time interval. For example, when the user is running, the rate of periodic movement may be a pace of the user, and when the user is biking, the rate of periodic movement may be a cadence of the user. The processor 120 may then determine a rate of distance travelled based on the rate of periodic movement and the type of the exerciser (e.g., the stride length of the user or current gear ratio of the user's bike). The processor 120 may determine a distance that the user has traveled during the first time interval based on the rate of periodic movement and the rate of distance traveled. The distance that the use has travelled may be used by the processor 120 in back-filling the route of the exercise. As such, the type of the exercise may be employed in certain implementations of the exercise route back-filling techniques described herein. Those skilled in the art would recognize that other combinations of various elements between the automatic exercise detection techniques, the automatic tracking or location information for the detected exercise, and the exercise route back-filling techniques may be possible.

Figure 8:
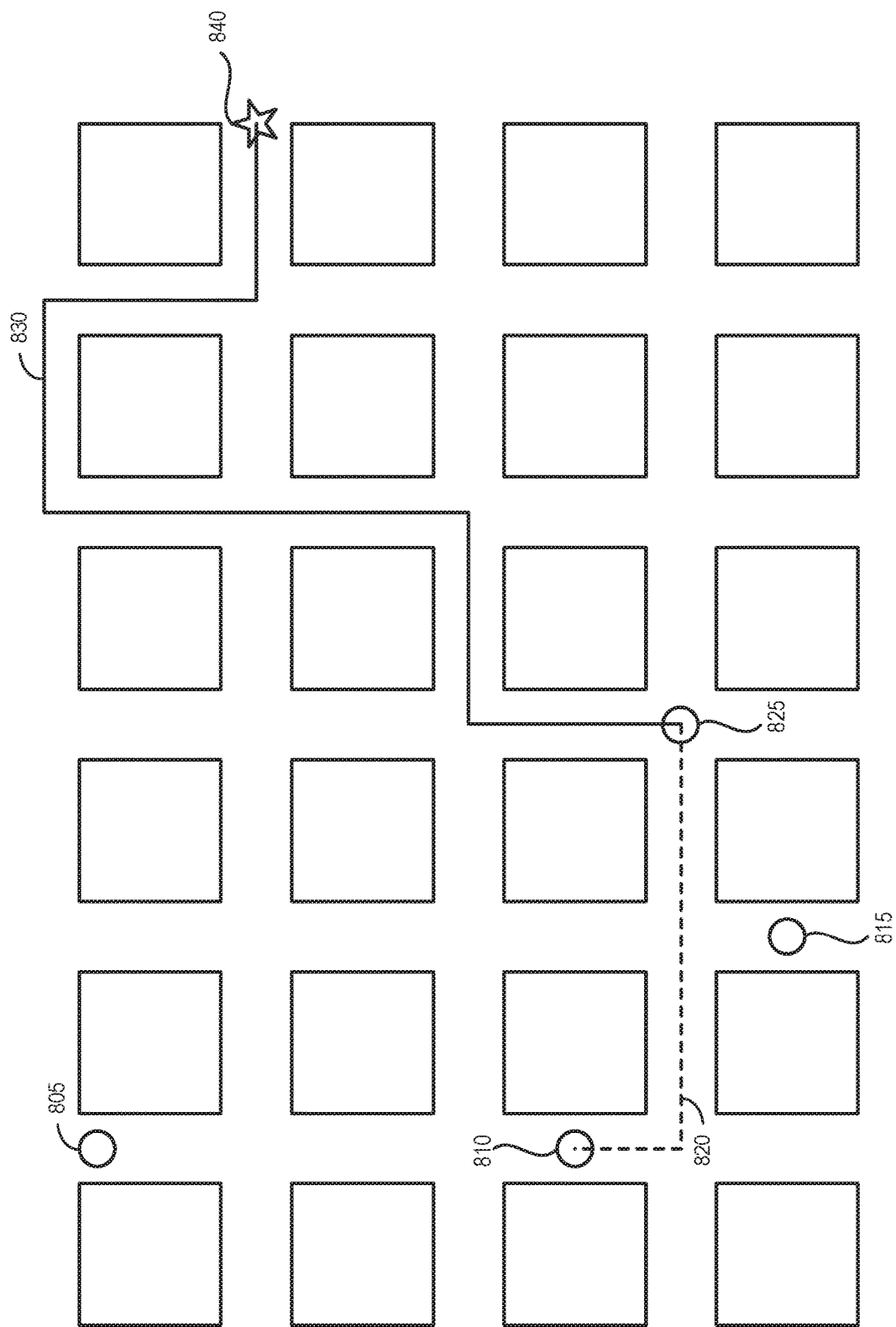
FIG. 8 is a block diagram illustrating an example implementation of the back-filling of an exercise route in accordance with aspects of this disclosure.

FIG. 8 is a block diagram illustrating an example implementation of the back-filling of an exercise route in accordance with aspects of this disclosure. Specifically, FIG. 8 illustrates a map including 6×4 city blocks. In the implementation of FIG. 8, the memory includes a plurality of candidate start locations 805, 810, and 815 stored therein. During the illustrated exercise, the user of the wearable device 100 begins an exercise near the candidate start location 810. The processor 120 of the wearable device 100 detects that the user has started the exercise (e.g., via a user input or automatically based on data received from one or more of the biometric sensor(s) 160). In response to detecting that the user has started the exercise, the processor 120 activates a geolocation sensor (e.g., the GPS receiver 166).

The processor 120 logs a first set of user data relating to at least one of distance, direction, and speed of the user during a first time interval. The first time interval may be the interval between the start of the exercise and a detected time of an initial location fix at point 825 (e.g., GPS fix). After the GPS fix at point 825, the processor 120 may log location information received from the geolocation sensor, which is indicated by the solid line 830. This logging of geolocation data may continue for a second time interval until the processor 120 detects the end of the exercise (e.g., via user input or the automatic detection of the end of the exercise) at the end point 840.

The processor 120 may back-fill the exercise either after the end of the exercise or concurrently with the exercise. For example, the processor 120 may estimate the exercise route 820 of the user during the first interval based on the first user data. When the processor 120 determines that the estimated route of the exercise is within a threshold distance from one of the stored candidate start locations (e.g., the candidate start location 810 in the illustrated example), the processor 120 may back-fill the route to the determined candidate start location. The back-filled route may thus include both the back-filled portion 820 and the GPS-generated portion 830 as an indication of the route travelled by the user during the exercise.

In some embodiments, the processor 120 may determine a second set of user data during a second time interval (e.g., GPS position, speed, and direction/heading based on multiple subsequent GPS fixes after an initial GPS fix), and combine that with a first set of user data regarding any detected turns (e.g., detected via directional sensors like gyroscopes and magnetometers) in a first time interval before the initial GPS fix, to thereby backtrack and determine the user's direction/heading throughout the first time interval (and ultimately where the user started the exercise). For example, if the second set of user data indicates the user is moving in a straight line heading east, and no turns were detected in the first time interval, then the processor 120 may infer that user was moving on that same line heading east throughout the first time interval. As another example, if the second set of user data indicates the user is moving in a straight line heading east, and one 90 degree right turn was detected in the first time interval, then the processor 120 may infer that user was initially moving north and then turned east during the first time interval. Thus, the processor 120 may utilize second time interval data (e.g., GPS-based heading data) to infer heading during the first time interval.

Figure 9:
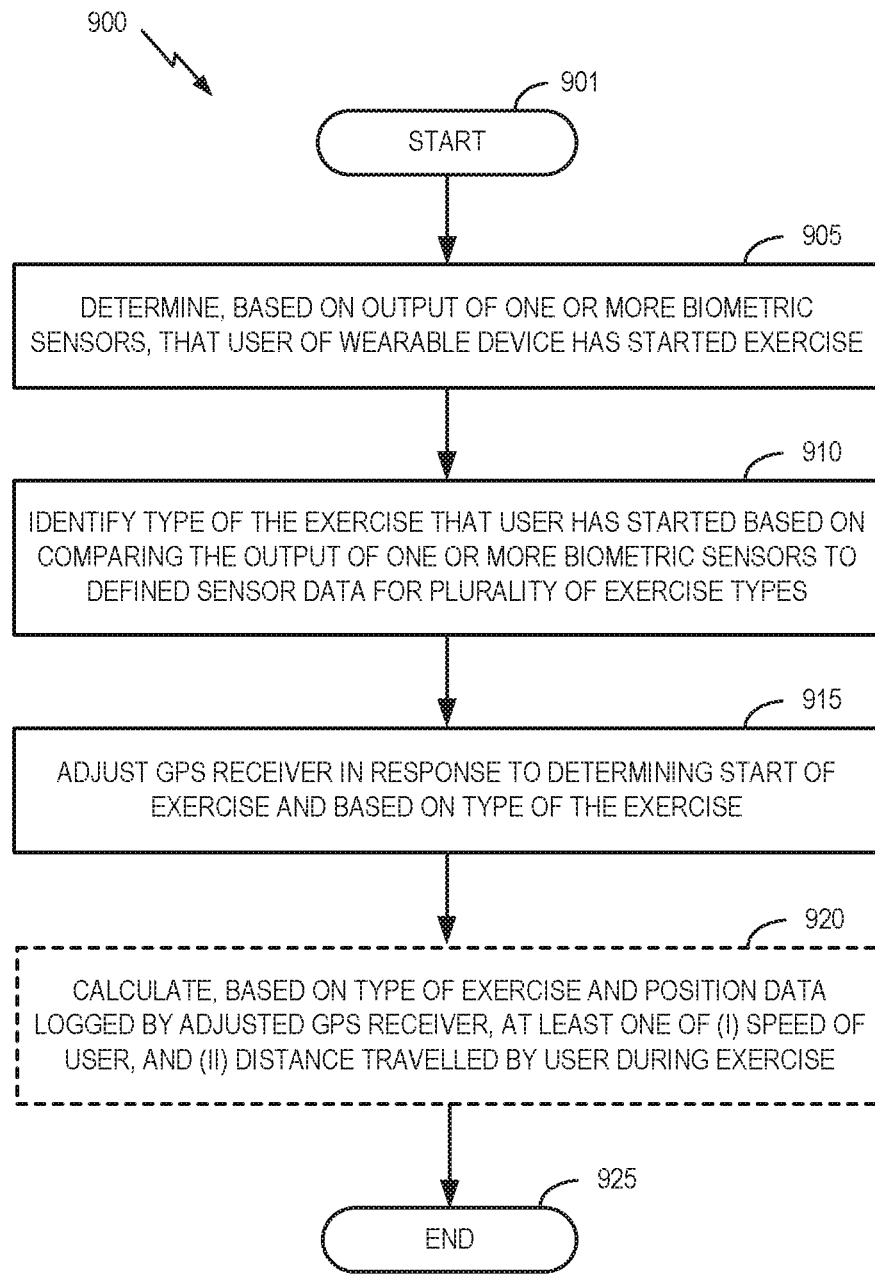
FIG. 9 is a flowchart illustrating another example method for automatic detection of exercise(s) and tracking of geolocation data in accordance with aspects of this disclosure.

Further Example Flowchart for Automatic Detection of Exercise(s) and Tracking of Geolocation Data FIG. 9 is a flowchart illustrating another example method operable by a wearable device 100, or component(s) thereof, for automatic detection of exercise(s) and tracking of geolocation data in accordance with aspects of this disclosure. For example, the steps of method 900 illustrated in FIG. 9 may be performed by a processor 120 of the wearable device 100. In another example, a client device 170 (e.g., a mobile phone) or a server 175 in communication with the wearable device 100 may perform at least some of the steps of the method 900. For convenience, the method 900 is described as performed by the processor 120 of the wearable device 100.

In one implementation, the wearable device 100 comprises one or more biometric sensors, a GPS receiver 166, and the processor 120. The method 900 begins at block 901. At block 905, the processor 120 determines, based on output of the one or more biometric sensors, that a user of the wearable device 100 has started an exercise. At block 910, the processor 120 identifies a type of the exercise that the user has started based on comparing the output of the one or more biometric sensors to defined sensor data for a plurality of exercise types. At block 915, the processor 120 adjusts the GPS receiver 166 in response to determining the start of the exercise and based on the type of the exercise.

In one implementation, after block 915, the method may involve, at block 920, the processor 120 calculating, based on the type of the exercise and positioned data logged by the adjusted GPS receiver 166, at least one of (i) a speed of the user, and (ii) a distance travelled by the user during the exercise. The method 900 ends at block 925.

Further Example Flowchart for Back-Filling of Geolocation-Based Exercise Route(s)

Figure 10:
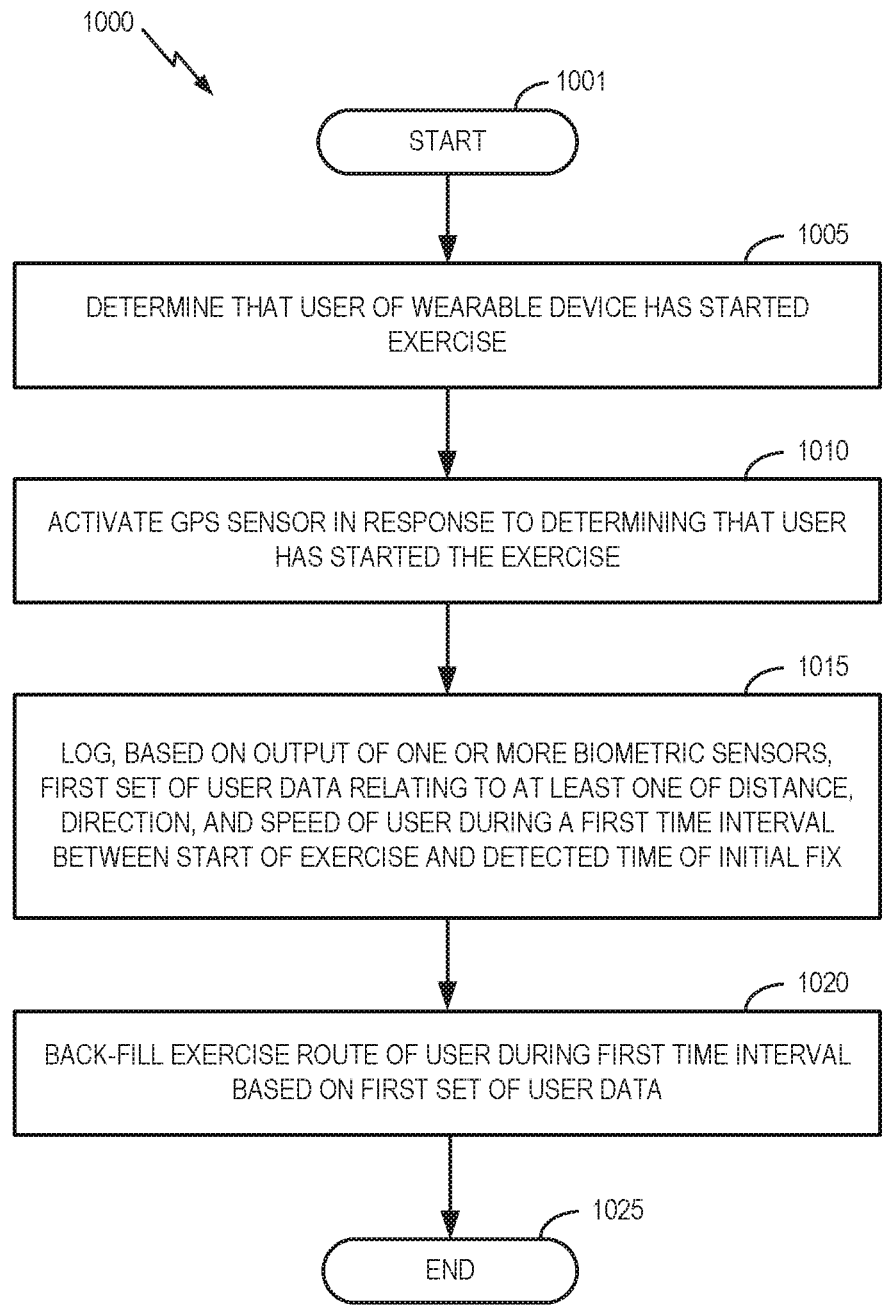
FIG. 10 is a flowchart illustrating another example method for back-filling of geolocation-based exercise route(s) in accordance with aspects of this disclosure.

FIG. 10 is a flowchart illustrating another example method operable by a wearable device 100, or component(s) thereof, for back-filling of geolocation-based exercise route(s) in accordance with aspects of this disclosure. For example, the steps of method 1000 illustrated in FIG. 10 may be performed by a processor 120 of the wearable device 100. In another example, a client device 170 (e.g., a mobile phone) or a server 175 in communication with the wearable device 100 may perform at least some of the steps of the method 1000. For convenience, the method 1000 is described as performed by the processor 120 of the wearable device 100.

In one implementation, the wearable device 100 comprises one or more biometric sensor(s) 160, a geolocation sensor (e.g., a GPS receiver 166), and the processor 120. The method 1000 begins at block 1001. At block 1005, the processor 120 determines that a user of the wearable device has started an exercise. At block 1010, the processor 120 activates the geolocation sensor in response to determining that the user has started the exercise. At block 1015, the processor 120 detects a time at which the geolocation sensor achieves an initial fix of a geolocation of the wearable device 100. At block 1020, the processor 120 logs, based on output of the one or more biometric sensors, a first set of user data relating to at least one of distance, direction, and speed of the user during a first time interval between the start of the exercise and the detected time of the initial fix. At block 1025, the processor 120 back-fills an exercise route of the user during the first time interval based on the first set of user data. The method 900 ends at block 1030.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure. However, the combinations of features between the respective embodiments are not necessarily limited thereto. Various embodiments of the disclosure have been described. These and other embodiments are within the scope of the following claims.

What is claimed is:

1. A method of operating a wearable device, the wearable device comprising one or more biometric sensors and a global positioning system (GPS) receiver, the method comprising:

determining that a user of the wearable device has started an exercise;

detecting a time at which the user has started the exercise in response to determining that the user of the wearable device has started the exercise;

activating the GPS receiver in response to determining that the user has started the exercise;

detecting a time at which the GPS receiver achieves an initial GPS fix of a location of the wearable device;

determining a first time interval between the time of the start of the exercise and the detected time of the initial GPS fix;

logging, based on output of the one or more biometric sensors, a first set of user data relating to at least one of distance, direction, and speed of the user during the first time interval; and back-filling an exercise route of the user during the first time interval based on the first set of user data.

2. The method of claim 1, wherein activating the GPS receiver comprises turning on the GPS receiver in response to determining that the user has started the exercise.

3. The method of claim 1, further comprising:
retrieving one or more candidate start locations of the exercise from a memory; and
identifying one of the one or more candidate start locations as a start location of the exercise,
wherein the back-filling comprises back-filling the exercise route from the location of the initial GPS fix to the identified start location of the exercise.

4. The method of claim 1, further comprising:
logging a second set of user data corresponding to position data from the GPS receiver collected during a second time interval after the initial GPS fix,
wherein the back-filling of the exercise route is further based on the second set of user data.

5. The method of claim 4, wherein:
the logging of the second set of user data comprises determining one or more second direction vectors representative of the user's movement during the second time interval based on the position data from the GPS receiver;
the logging of the first set of user data comprises determining one or more first direction vectors representative of the user's movement during the first time interval based on at least one of (i) output of the one or more biometric sensors and (ii) the second direction vectors; and
the back-filling of the exercise route is further based on the one or more of the first and second direction vectors.

6. The method of claim 1, further comprising:
retrieving a plurality of candidate start locations of the exercise from a memory;
logging a second set of user data corresponding to position data from the GPS receiver collected during a second time interval after the initial GPS fix; and
identifying one of the candidate start locations as a start location of the exercise based on the first and second sets of user data,
wherein the back-filling of the exercise route is further based on the second set of user data and the identified start location of the exercise.

7. The method of claim 6, wherein the memory is located in at least one of the wearable device, a paired mobile device, and a server.

8. The method of claim 1, further comprising:
logging a second set of user data corresponding to position data from the GPS receiver collected during a second time interval after the initial GPS fix; and
calibrating the first set of user data based at least in part on the second set of user data,
wherein the back-filling of the exercise route based on the first set of user data comprises back-filling of the exercise route based on the calibrated first set of user data.

9. The method of claim 8, wherein:
the logging of the first set of user data further comprises estimating a stride length of the user during the first time interval,
the logging of the second set of user data further comprising calculating a stride length of the user during the second time interval, and
the calibrating of the first set of user data comprises adjusting the estimated stride length during the first time interval based on the calculated stride length during the second time interval.

10. The method of claim 1, wherein the first set of user data comprises one or more of step count, step rate, stride length, cadence, and a distance-to-cadence ratio for the user.

11. The method of claim 1, further comprising:
receiving input from the user regarding at least one candidate start location; and
storing the at least one candidate start location in a memory.

12. The method of claim 1, wherein the back-filling comprises estimating a start location of the exercise based on the first set of user data, the method further comprising:
storing the estimated start location of the exercise in a memory; and
refining the estimated start location via clustering a plurality of previously stored start locations.

13. The method of claim 1, wherein the back-filling comprises:
estimating a start location of the exercise based on the first set of user data;
retrieving a plurality of candidate start locations of the exercise from a memory;
determining that the estimated start location is within a defined distance from one of the candidate start locations;
selecting the one of the candidate start locations in response to determining that the estimated start location is within the defined distance from the one of the candidate start locations; and
back-filling the exercise route between the selected candidate start location and the location of the initial GPS fix of the location of the wearable device.

14. The method of claim 1, wherein the determining that the user of the wearable device has started the exercise is based on output of the one or more biometric sensors.

15. The method of claim 1, wherein:
the logging of the first set of user data comprises determining one or more direction vectors representative of the user's movement during the first time interval based on output of the one or more biometric sensors; and
the back-filling of the exercise route is further based on the determined one or more direction vectors.

16. The method of claim 1, further comprising:
identifying a type of the exercise that the user has started based on comparing the output of the one or more biometric sensors to defined sensor data for a plurality of exercise types;
estimating a rate of periodic movement of the user during the first time interval; and
estimating a distance that the user has traveled during the first time interval based on the rate of periodic movement,
wherein the back-filling of the exercise route is further based on the distance that the user has traveled during the first time interval.

17. A wearable device, comprising:
one or more biometric sensors;
a global positioning system (GPS) receiver;
at least one processor coupled to the one or more biometric sensors and the GPS receiver; and
a memory storing computer-executable instructions for controlling the at least one processor to:
  determine that a user of the wearable device has started an exercise;
  detect a time at which the user has started the exercise in response to determining that the user has started the exercise;
  activate the GPS receiver in response to determining that the user has started the exercise;
  detect a time at which the GPS receiver achieves an initial GPS fix of a location of the wearable device;
  determine a first time interval between the time of the start of the exercise and the detected time of the initial GPS fix;
  determine, based on output of the one or more biometric sensors, a first set of user data relating to at least one of distance, direction, and speed of the user during a first time interval; and
  back-fill an exercise route of the user during the first time interval based on the first set of user data.

18. The wearable device of claim 17, wherein activating the GPS receiver comprises turning on the GPS receiver in response to determining that the user has started the exercise.

19. The wearable device of claim 17, wherein the memory further comprises computer-executable instructions for controlling the at least one processor to:
  retrieve one or more candidate start locations of the exercise from a memory; and
  identify one of the one or more candidate start locations as a start location of the exercise,
  wherein the back-filling comprises back-filling the exercise route from the location of the initial GPS fix to the identified start location of the exercise.

20. The wearable device of claim 17, wherein the memory further comprises computer-executable instructions for controlling the at least one processor to:
  determine, based on position data from the GPS receiver collected during a second time interval after the initial GPS fix, a second set of user data relating to locations of the wearable device during the second time interval,
  wherein the back-filling of the exercise route is further based on the second set of user data.

21. The wearable device of claim 17, wherein the memory further comprises computer-executable instructions for controlling the at least one processor to:
  retrieve at plurality of candidate start locations of the exercise from a memory;
  determine, based on position data from the GPS receiver collected during a second time interval after the initial GPS fix, a second set of user data relating to locations of the wearable device during the second time interval; and
  identify one of the candidate start locations as a start location of the exercise based on the first and second sets of user data,
  wherein the back-filling of the exercise route is further based on the second set of user data and the identified start location of the exercise.

22. A non-transitory computer readable storage medium having stored thereon instructions that, when executed, cause a processor of a wearable device to:
  determine that a user of the wearable device has started an exercise;
  detect a time at which the user has started the exercise in response to determining that the user of the wearable device has started the exercise;
  activate a global positioning system (GPS) receiver of the wearable device in response to determining that the user has started the exercise;
  detect a time at which the GPS receiver achieves an initial GPS fix of a location of the wearable device;
  determine a first time interval between the time of the start of the exercise and the detected time of the initial GPS fix;
  log, based on output of one or more biometric sensors of the wearable device, a first set of user data relating to at least one of distance, direction, and speed of the user during a first time interval; and
  back-fill an exercise route of the user during the first time interval based on the first set of user data.

23. The non-transitory computer readable storage medium of claim 22, wherein activating the GPS receiver comprises turning on the GPS receiver in response to determining that the user has started the exercise.

24. The non-transitory computer readable storage medium of claim 22, further having stored thereon instructions that, when executed, cause the processor to:
  retrieve one or more candidate start locations of the exercise from a memory; and
  identify one of the one or more candidate start locations as a start location of the exercise,
  wherein the back-filling comprises back-filling the exercise route from the location of the initial GPS fix to the identified start location of the exercise.

25. The non-transitory computer readable storage medium of claim 22, further having stored thereon instructions that, when executed, cause the processor to:
  log, based on position data from the GPS receiver collected during a second time interval after the initial GPS fix, a second set of user data relating to locations of the wearable device during the second time interval,
  wherein the back-filling of the exercise route is further based on the second set of user data.

26. The non-transitory computer readable storage medium of claim 22, further having stored thereon instructions that, when executed, cause the processor to:
  retrieve at plurality of candidate start locations of the exercise from a memory;
  log, based on position data from the GPS receiver collected during a second time interval after the initial GPS fix, a second set of user data relating to locations of the wearable device during the second time interval; and
  identify one of the candidate start locations as a start location of the exercise based on the first and second sets of user data,
  wherein the back-filling of the exercise route is further based on the second set of user data and the identified start location of the exercise.

27. The non-transitory computer readable storage medium of claim 22, further having stored thereon instructions that, when executed, cause the processor to:
  log, based on position data from the GPS receiver collected during a second time interval after the initial GPS fix, a second set of user data relating to at least one location of the wearable device during the second time interval; and calibrate the first set of user data based at least in part on the second set of user data, wherein the back-filling of the exercise route based on the first set of user data comprises back-filing of the exercise route based on the calibrated first set of user data.

28. A method of operating a wearable device, the wearable device comprising a geolocation sensor and one or more biometric sensors, the method comprising:

determining that a user of the wearable device has started an exercise;

activating the geolocation sensor in response to determining that the user has started the exercise;

detecting a time at which the user has started the exercise in response to determining that the user of the wearable device has started the exercise;

obtaining an initial geolocation fix of a location of the wearable device from the geolocation sensor;

detecting a time at which the geolocation sensor achieves the initial geolocation fix;

determining a first time interval between the time of the start of the exercise and the detected time of the initial geolocation fix;

logging, base on output of the one or more biometric sensors, a first set of user data relating to at least one of distance, direction, and speed of the user during the first time interval;

retrieving one or more candidate start locations of the exercise from a memory;

identifying one of the one or more candidate start locations as a start location of the exercise; and back-filling an exercise route of the user from the location of the initial geolocation fix to the identified start location of the exercise based on the first set of user data.

29. The method of claim 28, wherein activating the geolocation sensor comprises turning on the geolocation sensor in response to determining that the user has started the exercise.

* * * * *